US006284506B1

(12) United States Patent
Hoshino et al.

(10) Patent No.: US 6,284,506 B1
(45) Date of Patent: Sep. 4, 2001

(54) 3-HYDROXY-3-METHYLGLUTARYL-COA REDUCTASE POLYNUCLEOTIDES IN ISOPRENOID PRODUCTION

(75) Inventors: Tatsuo Hoshino, Kamakura; Kazuyuki Ojima; Yutaka Setoguchi, both of Fujisawa, all of (JP)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/306,595

(22) Filed: May 6, 1999

(30) Foreign Application Priority Data

May 6, 1998 (EP) .................................................. 98108210

(51) Int. Cl.[7] ...................................................... C12N 9/04
(52) U.S. Cl. .................. 435/190; 435/320.1; 435/252.3; 435/325; 435/254.11; 435/419; 435/67; 435/69.1; 536/23.1; 536/23.2
(58) Field of Search ................................ 536/23.1, 23.2; 435/320.1, 252.3, 325, 254.2, 254.11, 419, 190, 67, 69.1

(56) References Cited

FOREIGN PATENT DOCUMENTS

| 10-248575 | 9/1998 | (JP) . |
| WO 94/06918 | 3/1994 | (WO) . |
| WO 97/23633 | 7/1997 | (WO) . |

OTHER PUBLICATIONS

Croxen et al. Isolation of an Ustilago maydis gene encoding HMG–CoA reductase and expression of a C–terminal truncated form in Esherichia coli. Microbiology (1994) 140:2363–2370, 1994.*

GenBank Accession No. Z30085, Feb. 1994.*

Derwent English Language Abstract of JP 10–248575.

Wery, J. et al., "Structural and Phylogenetic Analysis of the Actin Gene from the Yeast *Phaffia rhodozyma*" *Yeast*, vol. 12, pp. 641–651 (1996).

Wery, J. et al., "High copy number integration into the ribosomal DNA of the yeast *Phaffia rhodozyma*" *Gene*, 184, pp. 89–97 (1997).

Shimada, H. et al., "Increased Carotenoid Production by the Food Yeast *Candida utilis* through Metabolic Engineering of the Isoprenoid Pathway" *Appl.& Env. Microbiol*, vol. 64, No. 7, pp. 2676–2680 (1998).

\* cited by examiner

*Primary Examiner*—Ponnathapu Achutamurthy
*Assistant Examiner*—Kathleen Kerr
(74) *Attorney, Agent, or Firm*—Mark E. Waddell; Stephen M. Haracz; Bryan Cave LLP

(57) ABSTRACT

The present invention relates to an isolated DNA sequence encoding an enzyme in the mevalonate pathway or the pathway from isopentenyl pyrophosphate to farnesyl pyrophosphate (i.e., HMG-CoA synthase, HMG-CoA reductase, mevalonate kinase, mevalonate pyrophosphate decarboxylase, and FPP synthase). Vectors and plasmids including such DNA, are also set forth. The invention also includes host cells transformed by such DNAs, or vectors or plasmids containing such DNAs. A process for the production of isoprenoids and carotenoids using such transformed host cells is also provided.

15 Claims, 2 Drawing Sheets

Biosynthetic pathway from acetyl-CoA to astaxanthin in *P. rhodozyma*

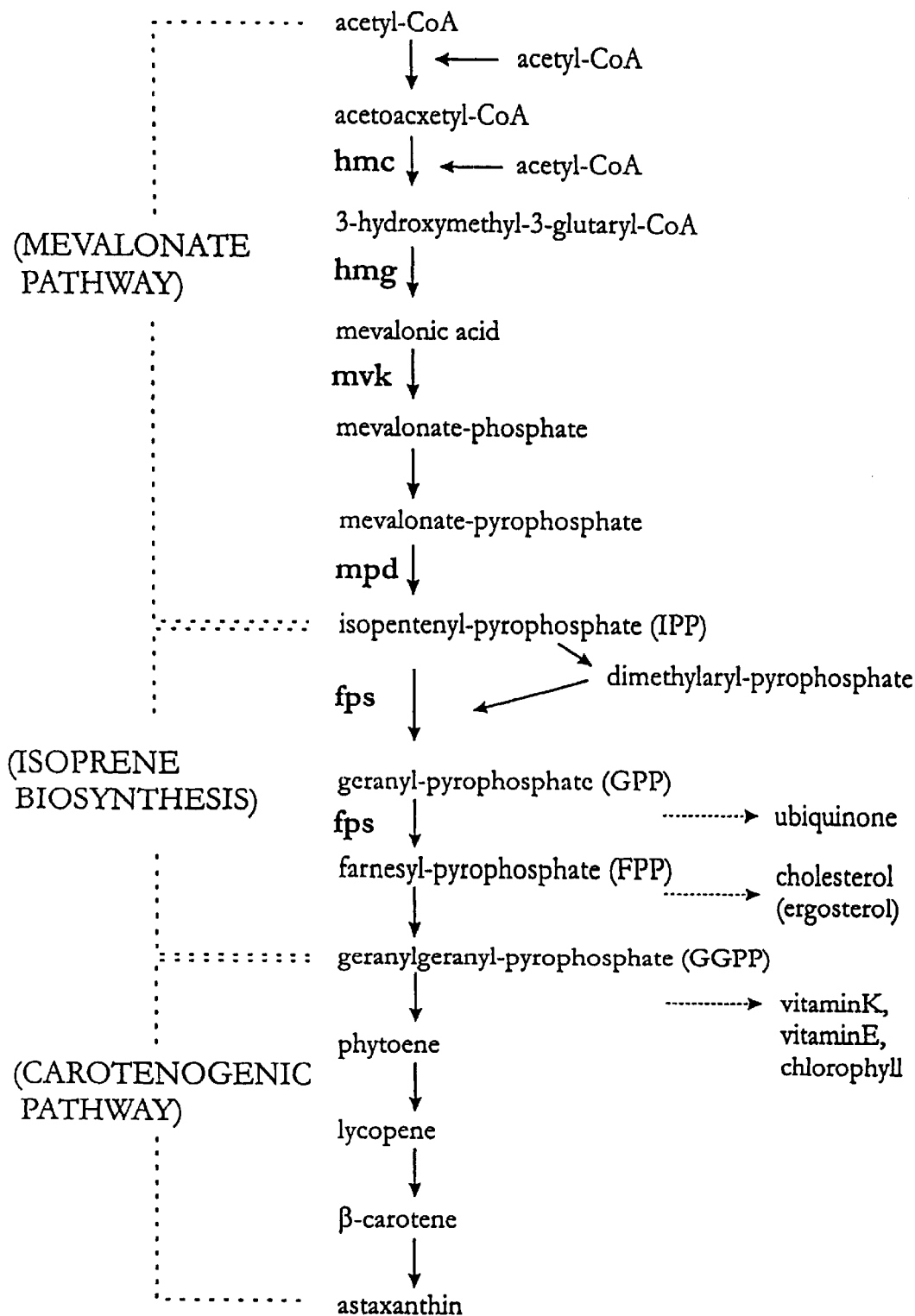
Fig. 1 Biosynthetic pathway from acetyl-CoA to astaxanthin in P. rhodozyma

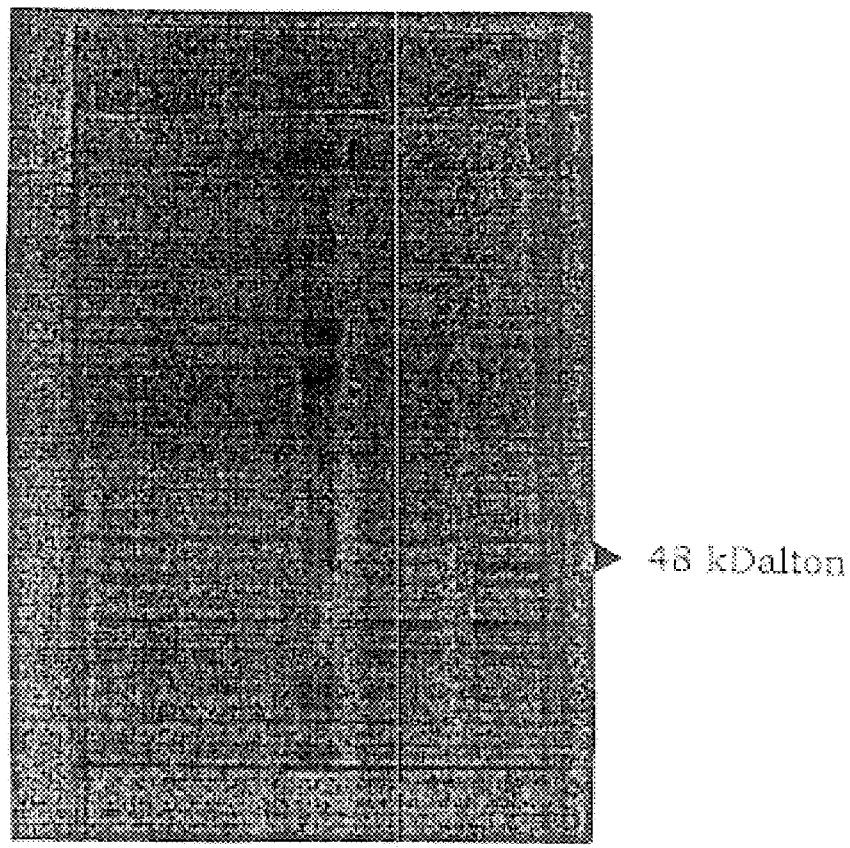
Fig. 2 Expression study of pseudo-mvk gene by insertion of one base

3-HYDROXY-3-METHYLGLUTARYL-COA REDUCTASE POLYNUCLEOTIDES IN ISOPRENOID PRODUCTION

FIELD OF THE INVENTION

The present invention relates to the manufacture of isoprenoids using molecular biology techniques. In particular, the present invention provides DNAs, vectors and host cells for the efficient production of various enzymes in the mevalonate pathway or for converting isopentyl pyrophosphate to farnesyl pyrophosphate synthase.

BACKGROUND OF THE INVENTION

Astaxanthin is reportedly distributed in a wide variety of organisms such as animals (e.g., birds, such as flamingo and scarlet ibis; fish, such as rainbow trout and salmon), algae and microorganisms. It is also reported that astaxanthin has a strong antioxidation property against oxygen radicals, which is believed to be pharmaceutically useful for protecting living cells against some diseases such as a cancer. Moreover, from a commercial prospective, there is an increasing demand for astaxanthin as a coloring reagent especially in the fish farming industry, such as salmon farming, because astaxanthin imparts a distinctive orange-red coloration to the fish and contributes to consumer appeal.

*Phaffia rhodozyma* is known as a carotenogenic yeast strain which produces astaxanthin specifically. Different from the other carotenogenic yeast, Rhodotorula species, such as *Phaffia rhodozyma* (*P. rhodozyma*) can ferment some sugars such as D-glucose. This is a commercially important feature. In a recent taxonomic study, the sexual cycle of *P. rhodozyma* was revealed and its telemorphic state was designated as *Xanthophyllomyces dendrorhous* (W. I. Golubev; Yeast 11, 101–110, 1995). Some strain improvement studies to obtain hyper-producers of astaxanthin from *P. rhodozyma* have been conducted, but such efforts have been restricted to conventional methods including mutagenesis and protoplast fusion in this decade.

Recently, Wery et al. reportedly developed a host vector system using *P. rhodozyma* in which a non-replicable plasmid was integrated into the genome of *P. rhodozyma* at the locus of a ribosomal DNA in multiple copies (Wery et al., Gene, 184, 89–97, 1997). Verdoes et al. reported vectors for obtaining a transformant of *P. rhodozyma*, as well as its three carotenogenic genes which code for the enzymes that catalyze the reactions from geranylgeranyl pyrophosphate to β-carotene (International patent WO97/23633).

It has been reported that the carotenogenic pathway from a general metabolite, acetyl-CoA consists of multiple enzymatic steps in carotenogenic eukaryotes as shown in FIG. 1. In this pathway, two molecules of acetyl-CoA are condensed to yield acetoacetyl-CoA which is converted to 3-hydroxy-3-methyglutaryl-CoA (HMG-CoA) by the action of 3-hydroxymethyl-3-glutaryl-CoA synthase. Next, 3-hydroxy-3-methylglutaryl-CoA reductase converts HMG-CoA to mevalonate, to which two molecules of phosphate residues are then added by the action of two kinases (mevalonate kinase and phosphomevalonate kinase). Mevalonate pyrophosphate is then decarboxylated by the action of mevalonate pyrophosphate decarboxylase to yield isopentenyl pyrophosphate (IPP) which becomes a building unit for a wide variety of isoprene molecules which are necessary in living organisms. This pathway is designated the "mevalonate pathway" taken from its important intermediate, mevalonate.

In this pathway, IPP is isomerized to dimethylaryl pyrophosphate (DMAPP) by the action of IPP isomerase. Then, IPP and DMAPP are converted to a $C_{10}$ unit, geranyl pyrophosphate (GPP) by a head to tail condensation. In a similar condensation reaction between GPP and IPP, GPP is converted to a $C_{15}$ unit, farnesyl pyrophosphate (FPP) which is an important substrate of cholesterol in animals, of ergosterol in yeast, and of the farnesylation of regulation proteins, such as the RAS protein. In general, the biosynthesis of GPP and FPP from IPP and DMAPP are catalyzed by one enzyme called FPP synthase (Laskovics et al., Biochemistry, 20, 1893–1901, 1981).

On the other hand, in prokaryotes such as eubacteria, isopentenyl pyrophosphate is reportedly synthesized in a different pathway via 1-deoxyxylulose-5-phosphate from pyruvate which is absent in yeast and animals (Rohmer et al., Biochem. J., 295, 517–524, 1993).

SUMMARY OF THE INVENTION

In studies of cholesterol biosynthesis, it was shown that the rate-limiting steps of cholesterol metabolism were in the steps of this mevalonate pathway, especially in its early steps catalyzed by HMG-CoA synthase and HMG-CoA reductase. It was recognized in accordance with the present invention that the biosynthetic pathways of cholesterol and carotenoid which share their intermediate pathway from acetyl-CoA to FPP can be used to improve the rate-limiting steps in the carotenogenic pathway. These steps may exist in the steps of mevalonate pathway, especially in the early mevalonate pathway such as the steps catalyzed by HMG-CoA synthase and HMG-CoA reductase. Improved yields of carotenoids, especially astaxanthin, are achievable using the process of the present invention.

In accordance with this invention, the genes and the enzymes involved in the mevalonate pathway from acetyl-CoA to FPP which are biological materials useful in improving the astaxanthin production process are provided. In the present invention, cloning and determination of the genes which code for HMG-CoA synthase, HMG-CoA reductase, mevalonate kinase, mevalonate pyrophosphate decarboxylase and FPP synthase is provided.

This invention also relates to the characterization of such enzymes as a result of the expression of such genes in suitable host organisms such as *E. coli*. These genes may be amplified in a suitable host, such as *P. rhodozyma*. The effects on carotenogenesis by these enzymes can be confirmed by cultivation of such a transformant in an appropriate medium under appropriate cultivation conditions.

In one embodiment, there is provided an isolated DNA sequence coding for at least one enzyme involved in the mevalonate pathway or the reaction pathway from isopentenyl pyrophosphate to farnesyl pyrophosphate. More specifically, such enzymes in accordance with the present invention are those having, for example, the following activities: 3-hydroxy-3-methylglutaryl-CoA synthase activity, 3-hydroxy-3-methylglutaryl-CoA reductase activity, mevalonate kinase activity, mevalonate pyrophosphate decarboxylase activity and farnesyl pyrophosphate synthase.

The isolated DNA sequences according to the present invention are more specifically characterized in that (a) they code for enzymes having amino acid sequences as set forth in SEQ ID NOs: 6, 7, 8, 9 and 10. The DNA sequences may alternatively (b) code for variants of such enzymes selected from (i) allelic variants and (ii) enzymes having one or more amino acid addition, insertion, deletion and/or substitution and having the stated enzyme activity.

Preferably, the isolated DNA sequence defined above is derived from a gene of *Phaffia rhodozyma*. Such a DNA sequence is represented in SEQ ID NOs: 1, 2, 4 and 5. This DNA sequence may also be an isocoding or an allelic variant for the DNA sequence represented in SEQ ID NOs: 1, 2, 4 and 5. In addition, this DNA sequence can be a derivative of a DNA sequence represented in SEQ ID NOs: 1, 2, 4 and 5 with addition, insertion, deletion and/or substitution of one or more nucleotide(s), and coding for a polypeptide having the above-referenced enzyme activity.

In the present invention, such derivatives can be made by recombinant means using one of the DNA sequences as disclosed herein by methods known in the art and disclosed, e.g. by Sambrook et al. (Molecular Cloning, Cold Spring Harbor Laboratory Press, New York, USA, second edition 1989) which is hereby incorporated by reference. Amino acid exchanges in proteins and peptides which do not generally alter the activity of the protein or peptide are known in the art and are described, for example, by H. Neurath and R. L. Hill in The Proteins (Academic Press, New York, 1979, see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, as well as these in reverse.

The present invention also provides an isolated DNA sequence coding for a polypeptide having mevalonate kinase activity, which DNA is selected from (i) a DNA sequence represented in SEQ ID NO: 3; (ii) an isocoding or an allelic variant for the DNA sequence represented in SEQ ID NO: 3; and (iii) a derivative of a DNA sequence represented in SEQ ID NO: 3 with addition, insertion, deletion and/or substitution of one or more nucleotide(s).

The present invention is intended to include those DNA sequences as specified above and as disclosed in the sequence listing, as well as their complementary strands, DNA sequences which include these sequences, DNA sequences which hybridize under standard conditions with such sequences or fragments thereof and DNA sequences, which because of the degeneracy of the genetic code, do not hybridize under standard conditions with such sequences, but which code for polypeptides having exactly the same amino acid sequence.

For purposes of the present invention, "standard conditions" for hybridization mean the conditions which are generally used by a one skilled in the art to detect specific hybridization signals and which are described, e.g. by Sambrook et al., supra. Preferably, the standard conditions are so called "stringent hybridization" and non-stringent washing conditions, more preferably so called stringent hybridization and stringent washing conditions. The stringency (high vs. low) of a particular hybridization will of course vary depending upon, for example, the salt concentration and temperature of the hybridization and washes, as well as the lengths of the probe and target DNAs. The examples provided herein set forth representative hybridization conditions but are not to be construed as limiting the scope of the invention.

Furthermore, DNA sequences which can be made by the polymerase chain reaction using primers designed on the basis of the DNA sequences disclosed herein by methods known in the art are also included in the present invention. It is understood that the DNA sequences of the present invention may also be made synthetically as described, e.g. in EP 747 483 which is hereby incorporated by reference.

Another embodiment of the present invention is a recombinant DNA, preferably a vector and/or a plasmid including a sequence coding for an enzyme functional in the mevalonate pathway or the reaction pathway from isopentenyl pyrophosphate to farnesyl pyrophosphate. The recombinant DNA vector and/or plasmid of the present invention includes regulatory regions, such as for example, promoters and terminators, as well as open reading frames of above named DNAs.

Another embodiment of the present invention is a process for transforming a host organism with a recombinant DNA, vector or plasmid. The recombinant organism of the present invention overexpresses a DNA sequence encoding an enzyme involved in the mevalonate pathway or the reaction pathway from isopentenyl pyrophosphate to farnesyl pyrophosphate. The host organism transformed with the recombinant DNA is intended to be used for, e.g., producing isoprenoids and carotenoids, in particular astaxanthin. Thus the present invention also includes such recombinant organisms/transformed hosts.

Another embodiment of the present invention is a method for the production of isoprenoids or carotenoids, preferably carotenoids, which includes cultivating recombinant organisms containing a DNA construct coding for such isoprenoids or carotenoids.

Another embodiment of the present invention is a method for producing an enzyme involved in the mevalonate pathway or the reaction pathway from isopentenyl pyrophosphate to farnesyl pyrophosphate. This method includes culturing a recombinant organism as mentioned above, under conditions conducive to the production of the enzyme. The method may also relate to obtaining the purified enzyme itself.

Another embodiment is a process for overexpressing an enzyme in the mevalonate pathway or an enzyme in the pathway for converting isopentenyl pyrophosphate to farnesyl pyrophosphate. This process includes selecting at least one DNA sequence from the group consisting of SEQ ID NOs: 1–5; transforming a host cell culture with at least one of the DNA sequences selected; expressing in the host cell at least one enzyme in the mevalonate pathway or an enzyme in the pathway for converting isopentenyl pyrophosphate to farnesyl pyrophosphate; and recovering the enzyme(s) from the culture.

The present invention will be understood more easily on the basis of the enclosed figures and the more detailed explanations given below.

BRIEF DESCRIPTION OF THE FIGURES

FIG. 1 depicts a deduced biosynthetic pathway from acetyl-CoA to astaxanthin in *P. rhodozyma*.

FIG. 2 shows the expression study by using an artificial mvk gene obtained from an artificial nucleotide addition at the amino terminal end of a pseudo-mvk gene from *P. rhodozyma*. The cells from 50 ml of broth were subjected to 10% sodium dodecyl sulfide-polyacrylamide gel electrophoresis (SDS-PAGE). Lane 1, *E. coli* (M15 (pREP4) (pQE30) without IPTG); Lane 2, *E. coli* (M15 (pREP4) (pQE30) with 1 mM IPTG); Lane 3, Molecular weight marker (105 kDa, 82.0 kDa, 49.0 kDa, 33.3 kD and 28.6 kDa, up to down, BIO-RAD); Lane 4, *E.coli* (M15 (pREP4) (pMK1209 #3334) without IPTG); Lane 5, *E.coli* (M15 (pREP4) (pMK1209 #3334) with 1 mM IPTG).

DETAILED DESCRIPTION OF THE INVENTION

The present invention provides an isolated DNA sequence which codes for enzymes which are involved in a biological pathway that includes the mevalonate pathway or the reaction pathway from isopentenyl pyrophosphate to farnesyl pyrophosphate. The enzymes of the present invention may be exemplified by those involved in the mevalonate pathway or the reaction pathway from isopentenyl pyrophosphate to farnesyl pyrophosphate in *Phaffia rhodozyma*. These sequences include, for example, 3-hydroxy-3-methylglutaryl-CoA synthase, 3-hydroxy-3-methylglutaryl-CoA reductase, mevalonate kinase, mevalonate pyrophosphate decarboxylase and farnesyl pyrophosphate synthase.

The present invention has utility in the production of the compounds involved in the mevalonate pathway and the carotenogenic pathway and various products derived from such compounds. The compounds involved in the mevalonate pathway are acetoacetyl-CoA, 3-hydroxymethyl-3-glutaryl-CoA, mevalonic acid, mevalonate-phosphate, mevalonate-pyrophosphate and isopentenyl-pyrophosphate. Subsequently, isopentenyl-pyrophosphate is converted to geranylgeranyl-pyrophosphate through geranyl-pyrophosphate and farnesyl-pyrophosphate via the "Isoprene Biosynthesis" reactions as indicated in FIG. 1.

The compounds involved in the carotenogenic pathway are geranylgeranylpyrophosphate, phytoene, lycopene, β-carotene and astaxanthin. Among the compounds involved in the above-mentioned biosynthesis, geranyl-pyrophosphate may be utilized for the production of ubiquinone. Farnesyl-pyrophosphate may be utilized for the production of sterols, such as cholesterol and ergosterol. Geranylgeranyl-pyrophosphate is used to produce vitamin K, vitamin E, chlorophyll and the like. Thus, the present invention has particular utility for the biological production of isoprenoids. As used herein, the term "isoprenoids" is intended to mean a series of compounds having an isopentenyl-pyrophosphate as a skeleton unit. Further examples of isoprenoids are vitamin A and vitamin $D_3$.

For purposes of the present invention, the term "DNA" is intended to mean a cDNA which contains only an open reading frame flanked between the short fragments in its 5'- and 3'-untranslated region and a genomic DNA which also contains its regulatory sequences, such as its promoter and terminator which are necessary for the expression of the gene of interest.

In general, a gene consists of several parts which have different finctions from each other. In eukaryotes, genes which encode a corresponding protein are transcribed to premature messenger RNA (pre-mRNA) differing from the genes for ribosomal RNA (rRNA), small nuclear RNA (snRNA) and transfer RNA (tRNA). Although RNA polymerase II (PolII) plays a central role in this transcription event, PolII cannot solely start transcription without a cis element covering an upstream region containing a promoter and an upstream activation sequence (UAS) and a trans-acting protein factor.

At first, a transcription initiation complex which consists of several basic protein components recognizes the promoter sequence in the 5'-adjacent region of the gene to be expressed. In this event, some additional participants are required in the case of the gene which is expressed under some specific regulation, such as a heat shock response, or adaptation to a nutrition starvation, etc. In such a case, a UAS is required to exist in the 5'-untranslated upstream region around the promoter sequence, and some positive or negative regulator proteins recognize and bind to the UAS. The strength of the binding of the transcription initiation complex to the promoter sequence is affected by such a binding of the trans-acting factor around the promoter. This enables regulation of the transcription activity.

After activation of a transcription initiation complex by phosphorylation, a transcription initiation complex initiates transcription from the transcription start site. Some parts of the transcription initiation complex are detached as an elongation complex which continues the transcription from the promoter region to the 3' direction of the gene (this step is called a promoter clearance event). The elongation complex continues transcription until it reaches a termination sequence that is located in the 3'-adjacent downstream region of the gene. Pre-mRNA thus generated is modified in the nucleus by the addition of a cap structure at the cap site which substantially corresponds to the transcription start site, and by the addition of polyA stretches at the polyA signal which is located at the 3'-adjacent downstream region. Next, intron structures are removed from the coding region and exon structures are combined to yield an open reading frame whose sequence corresponds to the primary amino acid sequence of a corresponding protein. This modification, in which a mature mRNA is generated, is necessary for stable gene expression.

As used herein, the term "cDNA" is intended to mean the DNA sequence which is reverse-transcribed from this mature mRNA sequence. It can be synthesized by the reverse transcriptase derived from viral species by using a mature mRNA as a template, experimentally.

To express a gene which was derived from a eukaryote, a procedure in which a cDNA is cloned into an expression vector in, for example, *E. coli*, is often used as shown in this invention. This procedure is used because intron structure specificity varies among eukaryotic organisms which results in an inability to recognize the intron sequence from that of other species. In fact, a prokaryote has no intron structure in its own genetic background. Even in the yeast, the genetic background is different between ascomycetea to which *Saccharomyces cerevisiae* belongs and basidiomycetea to which *P. rhodozyma* belongs. For example, Wery et al. showed that the intron structure of the actin gene from *P. rhodozyma* cannot be recognized nor spliced by the ascomycetous yeast, *Saccharomyces cerevisiae* (Yeast, 12, 641–651, 1996).

It has been reported that the intron structures of some genes involve regulation of their gene expressions (Dabeva, M. D. et al., Proc. Natl. Acad. Sci. U.S.A., 83, 5854, 1986). Therefore, it may be important to use a genomic fragment which still contains its introns in the case of self-cloning of a gene of interest whose intron structure involves such a regulation of its own gene expression.

To apply a genetic engineering method for a strain improvement study, it is necessary to study its genetic mechanism during, e.g., transcription and translation. It is also important to determine the genetic sequence of the gene, including for example, its UAS, promoter, intron structure and terminator in order to study the genetic mechanism.

According to this invention, the genes which code for the enzymes in the mevalonate pathway were cloned from genomic DNA of *P. rhodozyma*. The genomic sequence containing the HMG-CoA synthase (hmc) gene, the HMG-CoA reductase (hmg) gene, the mevalonate kinase (mvk) gene, the mevalonate pyrophosphate decarboxylase (mpd) gene and the FPP synthase (fps) gene including their 5'- and 3'-adjacent regions, as well as their intron structures were determined.

Initially, a partial gene fragment containing a portion of the hmc, hmg, mvk, mpd and fps genes was cloned using a degenerate PCR method. Using this degenerate PCR method, the gene of interest can be cloned which has a high amino acid sequence homology to the known enzyme from other species which has the same or similar function. A degenerate primer, which is used as a primer in degenerate PCR, was designed by reverse translation of the amino acid sequence to the corresponding nucleotides ("degenerated"). In such a degenerate primer, a mixed primer which consists of any of A, C, G or T, or a primer containing inosine at an ambiguous codon is generally used. In this invention, mixed primers were used as degenerate primers to clone the genes set forth above. In the present invention, the PCR conditions used can be varied depending on the primers used and genes cloned as described hereinafter.

An entire gene containing its coding region with its intron, as well as its regulation region, such as a promoter or a terminator can be cloned from a chromosome by screening a genomic library which is constructed in a vector such as a phage vector or a plasmid vector in an appropriate host cell using as a labeled probe a partial DNA fragment obtained by degenerate PCR as described above. In the present invention, a host strain such as $E.\ coli$, and a vector such as an $E.\ coli$ vector, a phage vector such as a λ phage vector, or a plasmid vector such as a pUC vector are used in the construction of a library and the following genetic manipulations such as a sequencing, a restriction digestion, a ligation and the like are carried out.

In this invention, an EcoRI genomic library of $P.\ rhodozyma$ was constructed in the derivatives of λ vector, λZAPII and λDASHII depending on the insert size. The insert size, i.e., the length of insert to be cloned, was determined by Southern blot hybridization for each gene before construction of a library. In this invention, the DNA probes were labeled with digoxigenin (DIG), a steroid hapten instead of a conventional $^{32}P$ label, using the protocol which was prepared by the supplier (Boehringer-Mannheim).

A genomic library constructed from the chromosome of $P.\ rhodozyma$ was screened using a DIG-labeled DNA fragment which contained a portion of the gene of interest as a probe. Hybridized plaques were picked up and used for further study. In the case of λDASHII (insert size was from 9 kb to 23 kb), prepared λDNA was digested by the restriction enzyme EcoRI, followed by cloning of the EcoRI insert into a plasmid vector, such as pUC19 or pBluescriptII SK+. When λZAPII was used in the construction of the genomic library, an in vivo excision protocol was conveniently used for the succeeding step of cloning the insert fragment into the plasmid vector using a derivative of a single stranded M13 phage, Ex assist phage (Stratagene). The plasmid DNA thus obtained was then sequenced.

In this invention, an automated fluorescent DNA sequencer (the ALFred system from Pharmacia) was used with an autocycle sequencing protocol in which the Taq DNA polymerase is employed in most cases of sequencing.

After determining the genomic sequence of each construct, the sequence of the coding region was used for cloning a cDNA of the corresponding gene. The PCR method was also used to clone cDNA fragments. PCR primers whose sequences were identical to the sequence at the 5'- and 3'-end of the open reading frame (ORF) were synthesized with the addition of an appropriate restriction site. Then, PCR was performed using those PCR primers.

In this invention, a cDNA pool was used as a template for PCR cloning of the cDNA. The cDNA pool included various cDNA species which were synthesized in vitro by viral reverse transcriptase and Taq polymerase (CapFinder Kit manufactured by Clontech was used) using the mRNA obtained from $P.\ rhodozyma$ as a template. Using this procedure, a corresponding cDNA was obtained and its identity was confirmed by its sequence. Furthermore, the cDNA was used to confirm its enzyme activity after cloning the cDNA fragment into an expression vector which functions in $E.\ coli$, under the strong promoter activity of, for example, the lac or T7 expression system.

Once enzyme activity of the expressed protein is confirmed, the protein is purified and used to raise monoclonal and/or polyclonal antibodies against the purified enzyme according to standard procedures in the art. These antibodies may be used to characterize the expression of the corresponding enzyme in a strain improvement study, an optimization study of the culture condition, and the like. Moreover, these antibodies may be used to purify large quantities of the enzyme in a single step using, for example, an affinity column.

In the present invention, after the rate-limiting step is determined in the biosynthetic pathway which consists of multiple enzymatic reactions, three strategies can be used to enhance the enzymatic activity of the rate-limiting reaction using its genomic sequence.

One strategy is to use the gene itself in its native form. The simplest approach is to amplify the genomic sequence including its regulation sequence such as a promoter and a terminator. This is realized by the cloning of the genomic fragment encoding the enzyme of interest into the appropriate vector on which a selectable marker that finctions in $P.\ rhodozyma$ is harbored.

A drug resistance gene which encodes the enzyme that enables the host to survive in the presence of a toxic antibiotic is often used for the selectable marker. The G418 resistance gene harbored in pGB-Ph9 (Wery et al. (Gene, 184, 89–97, 1997)) is an example of a drug resistance gene. A nutrition complementation marker may also be used in the host which has an appropriate auxotrophy marker. The $P.\ rhodozyma$ ATCC24221 strain which requires cytidine for its growth is one example of an auxotroph. By using CTP synthetase as donor DNA for ATCC24221, a host vector system using a nutrition complementation marker may be established.

In this system, two types of vectors may be used. One of the vectors is an integrated vector which does not have an autonomous replicating sequence. pGB-Ph9 is an example of this type of a vector. Because such a vector does not have an autonomous replicating sequence, it cannot replicate by itself and is present only in an integrated form on the chromosome of the host as a result of a single-crossing recombination using the homologous sequence between the vector and the chromosome. In case of increasing a dose of the integrated gene on the chromosome, amplification of the gene is often employed using a drug resistance marker. By increasing the concentration of the corresponding drug in the selection medium, only the strain which contains the integrated gene will survive. Using such a selection method, a strain containing the amplified gene may be selected.

Another type of vector is a replicable vector which has an autonomous replicating sequence. Such a vector can exist in a multicopy state which in turn allows the harbored gene to also exist in a multicopy state. By using such a strategy, an enzyme of interest which is coded by the amplified gene can be overexpressed.

Another strategy to overexpress an enzyme of interest is to place the gene of interest under a strong promoter. In such a strategy, the gene does not need to be in present a multicopy state. This strategy is also used to overexpress a gene of interest under the appropriate promoter whose promoter activity is induced in an appropriate growth phase and at an appropriate time during cultivation. For example, production of astaxanthin accelerates in the late phase of growth such as in the case of production of a secondary metabolite. Thus, the expression of carotenogenic genes may be maximized during the late phase of growth. In such a phase, gene expression of most biosynthetic enzymes decreases. Thus, for example, by placing a gene involved in the biosynthesis of a precursor of astaxanthin and whose expression is under the control of a vegetative promoter, such as a gene which encodes an enzyme involved in the mevalonate pathway, downstream of the promoter of the carotenogenic genes, all the genes involved in the biosynthesis of astaxanthin become synchronized in their timing and phase of expression.

Another strategy to overexpress an enzyme of interest is to induce a mutation in its regulatory elements. For this purpose, a kind of reporter gene such as a β-galactosidase gene, a luciferase gene (a gene coding a green fluorescent protein), and the like is inserted between the promoter and the terminator sequence of the gene of interest so that all the parts including promoter, terminator and the reporter gene are fused and function with each other.

For example, transformed P. rhodozyma in which the reporter gene is introduced on the chromosome or on the vector is mutagenized in vivo to induce a mutation within the promoter region of the gene of interest. The mutation is monitored, for example, by detecting a change in activity coded for by the reporter gene. If the mutation occurs in a cis element of the gene, the mutation point would be determined by the rescue of the mutagenized gene and subsequent sequencing. The determined mutation is introduced to the promoter region on the chromosome by recombination between a native promoter sequence and a mutated sequence. In the same procedure, the mutation occurring in the gene which encodes a trans-acting factor can be also obtained. It would also affect the overexpression of the gene of interest.

A mutation may also be induced by in vitro mutagenesis of a cis element in the promoter region. In this approach, a gene cassette, containing a reporter gene fused to a promoter region derived from a gene of interest at its 5'-end and a terminator region from a gene of interest at its 3'-end, is mutagenized and then introduced into P. rhodozyma. By detecting the difference in the activity of the reporter gene, an effective mutation can be screened and identified. Such a mutation can be introduced in the sequence of the native promoter region on the chromosome by the same methods used for in vivo mutation.

As a donor DNA, a gene which encodes an enzyme of the mevalonate pathway or FPP synthase is introduced alone or co-introduced on a plasmid vector. A coding sequence which is identical to its native sequence, as well as its allelic variant (a sequence which has one or more amino acid additions, deletions and/or substitutions) can be used so long as its corresponding enzyme has the stated enzyme activity. Such a vector is introduced into P. rhodozyma by transformation and a transformant is selected by spreading the transformed cells on an appropriate selection medium such as, for example, YPD agar medium containing genetic in the case of pGB-Ph9 as a vector or a minimal agar medium omitting cytidine when the auxotroph ATCC24221 is used as a recipient.

Such a genetically engineered P. rhodozyma is cultivated in an appropriate medium and evaluated for its production of astaxanthin. A hyper-producer of astaxanthin thus selected may be confirmed in view of the relationship between its productivity and the level of gene or protein expression which is introduced by such a genetic engineering method.

Thus in the present invention, all three strategies may be used to enhance the enzymatic activity of the rate limiting step in the enzymatic pathways set forth above.

The following examples are set forth to illustrate compositions and processes of the present invention. These examples are provided for purposes of illustration only and are not intended to be limiting in any sense.

EXAMPLES

The following materials and methods were employed in the examples described below:

Strains

P. rhodozyma ATCC96594 (This strain was redeposited on Apr. 8, 1998 pursuant to the Budapest Treaty and was assigned accession No. 74438).

E. coli DH5α: F$^-$, φ80d, lacZΔDM15, Δ(lacZYA-argF) U169, hsd($r_K^-$, $m_K^+$), recA1, endA1, deoR, thi-1, supE44, gyrA96, relA1 (Toyobo)

E. coli XL1-Blue MRF': Δ(mcrA)183, Δ(mcrCB-hsdSMR-mrr)173, endA1, supE44, thi-1, recA1, gyrA96, relA1, lac[F' proAB, lacI$^q$ZΔM15, Tn10 (tet$^r$)] (Stratagene)

E. coli SOLR: e14$^-$(mcrA), Δ(mcrCB-hsdSMR-mrr)171, sbcC, recB, recJ, umuC:: Tn5(kan$^r$), uvrC, lac, gyrA96, relA1, thi-1, endA1, $λ^R$, [F' proAB, lacI$^q$Z ΔM15] Su$^-$(nonsuppressing) (Stratagene, Calif., USA)

E. coli XL1 MRA (P2): Δ(mcrA)183, Δ(mcrCB-hsdSMR-mrr)173, endA1, supE44, thi-1, gyrA96, relA1, lac (P2 lysogen) (Stratagene)

E. coli BL21 (DE3) (pLysS): dcm$^-$, ompTr$_B^-$m$_B^-$Ion$^-$λ (DE3), pLysS (Stratagene)

E. coli M15 (pREP4)(QIAGEN)(Zamenhof P. J. et al., J. Bacteriol. 110, 171–178, 1972)

E. coli KB822:pcnB80, zad:: Tn10, Δ(lacU169), hsdR17, endA1, thi-1, supE44

E. coli TOP10: F$^-$, mcrA, Δ(mrr-hsdRMS-mcrBC), φ80, ΔlacZ M15, ΔlacX74, recA1, deoR, araD139, (ara-leu) 7697, galU, galK, rpsL (Str$^r$), endA1, nupG (Invitrogen)

Vectors

λZAPII (Stratagene)

λDASHII (Stratagene)

pBluescriptII SK+(Stratagene)

pUC57 (MBI Fermentas)

pMOSBlue T-vector (Amersham)

pET4c (Stratagene)

pQE30 (QIAGEN)

pCR2.1TOPO (Invitrogen)

Media

P. rhodozyma strain is maintained routinely in YPD medium (DIFCO). E. coli strain is maintained in LB medium (10 g Bacto-trypton, 5 g yeast extract (DIFCO) and 5 g NaCl per liter). NZY medium (5 g NaCl, 2 g MgSO$_4$—7H$_2$O, 5 g yeast extract (DIFCO), 10 g NZ amine type A (Sheffield) per liter) is used for phage propagation in a soft agar (0.7% agar (WAKO)). When an agar medium was prepared, 1.5% of agar (WAKO) was supplemented.

Methods

General methods of molecular genetics were practiced according to Molecular Cloning: a Laboratory Manual, 2nd Edition (Cold Spring Harbor Laboratory Press, 1989). Restriction enzymes and T4 DNA ligase were purchased from Takara Shuzo (Japan).

Isolation of chromosomal DNA from *P. rhodozyma* was performed using a QIAGEN Genomic Kit (QIAGEN) following the protocol supplied by the manufacturer. Mini-preps of plasmid DNA from transformed *E. coli* were performed with the Automatic DNA isolation system (PI-50, Kurabo, Co. Ltd., Japan). Midi-preps of plasmid DNA from an *E. coil* transformant were performed using a QIAGEN column (QIAGEN). Isolation of λDNA was performed with the Wizard lambda preps DNA purification system (Promega) following the protocol of the manufacturer. A DNA fragment was isolated and purified from agarose using QIAquick or QIAEX II (QIAGEN). Manipulation of λ phage derivatives was done according to the protocol of the manufacturer (Stratagene).

Isolation of total RNA from *P. rhodozyma* was performed by the phenol method using Isogen (Nippon Gene, Japan). mRNA was purified from total RNA thus obtained using a mRNA separation kit (Clontech). cDNA was synthesized using a CapFinder CDNA construction kit (Clontech).

In vitro packaging was performed using Gigapack III gold packaging extract (Stratagene).

Polymerase chain reaction (PCR) was performed with a thermal cycler from Perkin Elmer model 2400. Each PCR condition is described in the examples. PCR primers were purchased from a commercial supplier or synthesized with a DNA synthesizer (model 392, Applied Biosystems). Fluorescent DNA primers for DNA sequencing were purchased from Pharmacia. DNA sequencing was performed with the automated fluorescent DNA sequencer (ALFred, Pharmacia).

Competent cells of DH5 were purchased from Toyobo (Japan). Competent cells of M15 (pREP4) were prepared by the $CaCl_2$ method described by Sambrook et al. (Molecular Cloning: A Laboratory Manual, 2nd Edition, Cold Spring Harbor Laboratory Press, 1989).

Example 1

Isolation of mRNA from *P. rhodozyma* and Construction of cDNA Library

To construct a cDNA library of *P. rhodozyma*, total RNA was isolated by phenol extraction right after cell disruption. The mRNA from the *P. rhodozyma* ATCC96594 strain was purified using a mRNA separation kit (Clontech).

*P. rhodozyma* cells (ATCC96594 strain) from 10 ml of a two-day-culture in YPD medium were harvested by centrifugation (1500×g for 10 min.) and washed once with extraction buffer (10 mM Na-citrate/HCl (pH 6.2) containing 0.7 M KCl). After suspending the cells in 2.5 ml of extraction buffer, the cells were disrupted by a French press homogenizer (Ohtake Works Corp., Japan) at 1500 $kgf/cm^2$ and immediately mixed with 2× volumes of isogen (Nippon gene) according to the method specified by the manufacturer. In this step, 400 µg of total RNA was recovered.

This total RNA was purified using a mRNA separation kit (Clontech) according to the method specified by the manufacturer. Using this method, 16 µg of mRNA from *P. rhodozyma* ATCC96594 strain was obtained.

To construct a cDNA library, a CapFinder PCR cDNA construction kit (Clontech) was used according to the method specified by the manufacturer. One µg of purified mRNA was applied for a first strand synthesis followed by PCR amplification. After this PCR amplification, 1 mg of a cDNA pool was obtained.

Example 2

Cloning of the Partial hmc (3-hydroxy-3-methylglutaryl-CoA synthase) Gene from *P. rhodozyma*

To clone a partial hmc gene from *P. rhodozyma*, a degenerate PCR method was exploited. Two mixed primers whose nucleotide sequences were designed and synthesized (as shown in TABLE 1) based on the common sequence of known HMG-CoA synthase genes from other species.

Table 1

Sequence of Primers Used in the Cloning of the hmc Gene

Hmgs1; GGNAARTAYACNATHGGNYTNGGNCA (sense primer) (SEQ ID NO: 11)
Hmgs3; TANARNSWNSWNGTRTACATRTTNCC (antisense primer) (SEQ ID NO: 12)
(N=A, C, G or T; R=A or G, Y=C or T, H=A, T or C, S=C or G, W=A or T)

After a PCR reaction of 25 cycles at 95° C. for 30 seconds, 50° C. for 30 seconds and 72° C. for 15 seconds using ExTaq (Takara Shuzo) as a DNA polymerase and the cDNA pool obtained in example 1 as a template, the resulting reaction mixture was separated by electrophoresis on an agarose gel. A PCR band that has the desired length was recovered and purified by QIAquick (QIAGEN) according to the method of the manufacturer and then ligated to pMOSBlue T-vector (Amersham). After transformation of competent *E. coli* DH5α cells with the isolated DNA, 6 white colonies were selected and plasmids were isolated with an Automatic DNA isolation system (Kurabo). As a result of sequencing, it was found that the clone had a sequence whose deduced amino acid sequence was similar to known hmc genes. This isolated cDNA clone was designated as pHMC211 and used for further study.

Example 3

Isolation of Genomic DNA from *P. rhodozyma*

To isolate a genomic DNA from *P. rhodozyma*, a QIAGEN genomic kit was used according to the method specified by the manufacturer.

At first, the *P. rhodozyma* ATCC96594 strain cells from 100 ml of an overnight culture in YPD medium were harvested by centrifugation (1500×g for 10 min.) and washed once with TE buffer (10 mM Tris/HCl (pH 8.0) containing 1 mM EDTA). After suspending the cells in 8 ml of Y1 buffer of the QIAGEN genomic kit, lyticase (SIGMA) was added at the concentration of 2 mg/ml to disrupt the cells by enzymatic degradation. This reaction mixture was incubated for 90 minutes at 30° C. and then proceeded to the next extraction step. Finally, 20 µg of genomic DNA was obtained.

Example 4

Southern Blot Hybridization Using pHMC211 as a Probe

Southern blot hybridization was performed to clone a genomic fragment which contains the hmc gene from *P. rhodozyma*. Two µg of genomic DNA from example 3 was digested by EcoRI and subjected to agarose gel electrophoresis followed by acidic and alkaline treatment. The denatured DNA was transferred to a nylon membrane (Hybond N+, Amersham) using a transblot (Joto Rika) apparatus for an hour. The DNA which was transferred to the nylon membrane was fixed thereto with heat (80° C., 90 minutes). A probe was prepared by labeling template DNA (EcoRI- and SalI-digested pHMC211) using the DIG multipriming method (Boehringer Mannheim).

Hybridization was performed with the method specified by the manufacturer (Boehringer Mannheim). The hybridization experiment was performed using a commercially available DIG (digoxigenin) labeling kit and luminescent detection kit (Boehringer Mannheim, Mannheim, Germany). Standard hybridization conditions were used as follows: The hybridization solution contained formamide (WAKO) 50% (V/V), blocking reagent (Boehringer Mannheim) 2% (W/V), 5×SSC, N-lauroylsarcosine 0.1% (W/V), and SDS 0.3% (W/V). The hybridization was performed at 42° C. overnight. Washing and luminescent detection was performed according to the protocol supplied by the manufacturer. For example, the following standard post hybridization washing routine may be used: wash the nylon membrane twice for 5 minutes each in 2×SSC and 0.1% SDS at room temperature followed by 2 washes of 15 minutes each in 0.1 SSC and 0.1% SDS at 68° C. under constant agitation. These washing conditions may be varied as is known in the art depending upon the DNA, probe and intended result. In the present example, a hybridized band was visualized in the range from 3.5 to 4.0 kilobases (kb).

Example 5

Cloning of a Genomic Fragment Containing hmc Gene

Four μg of the genomic DNA from Example 3 was digested with EcoRI and subjected to agarose gel electrophoresis. Then, DNAs whose length is within the range from 3.0 to 5.0 kb were recovered using a QIAEX II gel extraction kit (QIAGEN) according to the method specified by the manufacturer. The purified DNA was ligated to 1 μg of EcoRI-digested and CIAP (calf intestine alkaline phosphatase) -treated λZAPII (Stratagene) at 16° C. overnight, and packaged by Gigapack III gold packaging extract (Stratagene). The packaged extract was used to infect an E. coli XL1Blue MRF' strain and over-laid with NZY medium poured onto LB agar medium. About 6000 plaques were screened using an EcoRI- and SalI-digested pHMC211 fragment as a probe. Two plaques were hybridized to the labeled probe and subjected to the in vivo excision protocol according to the method specified by the manufacturer (Stratagene). It was found that isolated plasmids had the same fragments in the opposite direction to each other based on restriction analysis and sequencing. As a result of sequencing, the obtained EcoRi fragment contained the same nucleotide sequence as that of the pHMC211 clone. One of these plasmids was designated pHMC526 and used for further study. A complete nucleotide sequence was obtained by sequencing deletion derivatives of pHMC526, and sequencing with a primer-walking procedure.

Using these methods, it was determined that the insert fragment of pHMC526 consists of 3,431 nucleotides that contained 10 complete exons and one incomplete exon and 10 introns with about 1 kb of 3'-terminal untranslated region.

Example 6

Cloning of Upstream Region of hmc Gene

Cloning of the 5'-region adjacent to the hmc gene was performed using a Genome Walker Kit (Clontech) because pHMC 526 does not contain its 5' end of hmc gene. As a first step, the PCR primers whose sequences were shown in Table 2 were synthesized.

Table 2

Sequence of Primers Used in the Cloning of the 5'-region Adjacent to the hmc Gene Hmc21; GAAGAACCCCATCAAAAGCCTCGA (primary primer) (SEQ ID NO: 13)
Hmc22; AAAAGCCTCGAGATCCTTGTGAGCG (nested primer) (SEQ ID NO: 14)

Protocols for the genomic library construction and the PCR conditions were the same as those specified by the manufacturer using the genomic DNA preparation obtained in Example 3 as a PCR template. The PCR fragments that had an EcoRV site at the 5' end (0.45 kb), and that had a PvuII site at the 5' end (2.7 kb) were recovered and cloned into pMOSBlue T-vector using E. coli DH5α as a host strain. By sequencing 5 independent clones from both constructs, it was confirmed that the 5' region adjacent to the hmc gene was cloned and a small part (0.1 kb) of an EcoRI fragment within its 3' end was found. The clone obtained by the PvuII construct in the above experiment was designated as pHM-CPv708 and used for further study.

Next, Southern blot analysis was performed using the method set forth in Example 4. The 5'-region adjacent to the hmc gene contained in the 3 kb EcoRI fragment was determined. After construction of a 2.5 to 3.5 kb EcoRI library in λZAPII, 600 plaques were screened and 6 positive clones were selected. As a result of the sequencing of these 6 clones, it was found that 4 clones within 6 positive plaques had the same sequence as that of the pHMCPv708. One of those clones was named pHMC723 and was used for further analysis.

The PCR primers whose sequences are set forth in TABLE 3 below were synthesized and used to clone a small (0.1 kb) EcoRI fragment located between the 3.5 kb and 3.0 kb EcoRI fragments on the chromosome of P. rhodozyma.

Table 3

Sequence of Primers Used in Cloning the Small EcoRI Portion of the hmc Gene

Hmc30; AGAAGCCAGAAGAGAAAA (sense primer) (SEQ ID NO: 15)
Hmc31; TCGTCGAGGAAAGTAGAT (antisense primer) (SEQ ID NO: 16)

The PCR conditions used were the same as shown in Example 2. An amplified fragment (0.1 kb in length) was cloned into pMOSBlue T-vector and used to transform E. coli DH5α. Plasmids were prepared from 5 independent white colonies and subjected to sequencing.

Using the sequence information, it was determined that the nucleotide sequence (4.8 kb) contained the hmc gene (SEQ ID NO: 1). The coding region was 2,432 base pairs in length and consisted of 11 exons and 10 introns. Introns were scattered throughout the coding region without 5' or 3' bias. It was found also that the open reading frame consists of 467 amino acids (SEQ ID NO: 6) whose sequence is strikingly similar to the known amino acid sequence of HMG-CoA synthase gene from other species (49.6% identity to HMG-CoA synthase from *Schizosaccharomyces pombe*).

Example 7

Expression of hmc Gene in E. coli and Confirmation of its Enzymatic Activity

The PCR primers whose sequences are set forth in TABLE 4 below were synthesized to clone a cDNA fragment of the hmc gene.

Table 4

Sequence of Primers Used in the Cloning of cDNA of hmc Gene

Hmc25; GGTACCATATGTATCCTTCTACTACCGAAC (sense primer) (SEQ ID NO: 17)
Hmc26; GCATGCGGATCCTCAAGCAGAAGGGACCTG (antisense primer) (SEQ ID NO: 18)

The PCR conditions were as follows; 25 cycles at 95° C. for 30 seconds, 55° C. for 30 seconds and 72° C. for 3 minutes. As a template, 0.1 μg of the cDNA pool obtained in Example 2 was used, and Pfu polymerase was used as a DNA polymerase. An amplified 1.5 kb fragment was recovered and cloned in pT7Blue-3 vector (Novagen) using a perfectly blunt cloning kit (Novagen) according to the protocol specified by the manufacturer.

Six independent clones from white colonies of E. coli DH5α transformants were selected and plasmids were prepared from those transformants. As a result of restriction analysis, 2 clones were selected for further characterization by sequencing. One clone has an amino acid substitution at position 280 (from glycine to alanine) and the other clone has a substitution at position 53 (from alanine to threonine). Alignment of amino acid sequences derived from known hmc genes showed that the alanine and glycine residues at position 280 were observed in all the sequences from other species. This fact suggested that an amino acid substitution at position 280 would not affect its enzymatic activity. This clone (mutant at position 280) was selected and designated pHMC731 for a succeeding expression experiment.

Next, a 1.5 kb fragment obtained by NdeI- and BamHI-digestion of pHMC731 was ligated to pET11c (Stratagene) digested by the same pairs of restriction enzymes, and introduced into E. coli DH5α. As a result of restriction analysis, a plasmid that had a correct structure (pHMC818) was recovered. Then, competent E. coli BL21 (DE3) (pLysS) cells (Stratagene) were transformed with the plasmid (pHMC818), and one clone that had a correct structure was selected for further study.

For an expression study, strain BL21 (DE3) (pLysS) (pHMC818) and a vector control strain BL21 (DE3) (pLysS) (pET11c) were cultivated in 100 ml of LB medium at 37° C. until an OD of 0.8 at 600 nm was reached (about 3 hours) in the presence of 100 μg/ml of ampicillin. Then, the broth was divided into two samples of the same volume, and then 1 mM of isopropyl β-D-thiogalactopyranoside (IPTG) was added to one sample (induced). Cultivation of both samples was continued for another 4 hours at 37° C. Twenty five μl of broth was removed from induced- and uninduced-cultures of the hmc clone and the vector control cultures and subjected to sodium dodecyl sulfate-polyacrylamide gel electrophoresis (SDS-PAGE) analysis. It was confirmed that a protein whose size was similar to the deduced molecular weight based on the nucleotide sequence (50.8 kDa) was expressed only in the case of the clone that was harbored in pHMC818 with the induction.

Cells from 50 ml of broth were harvested by centrifugation (1500×g, 10 minutes), washed once and suspended in 2 ml of hmc buffer (200 mM Tris-HCl (pH 8.2)). The cells were disrupted by a French press homogenizer (Ohtake Works) at 1500 kgf/cm² to yield a crude lysate. After centrifugation of the crude lysate, a supernatant fraction was recovered and used as a crude extract for enzymatic analysis. Only in the case of the lysate from the induced clone (pHMC818), was a white pellet spun down and recovered. An enzyme assay for 3-hydroxy-3-methylglutaryl-CoA (HMG-CoA) synthase was performed using the photometric assay according to the method by Stewart et al. (J. Biol. Chem. 241(5), 1212–1221, 1966). In the crude extract, the activity of 3-hydroxy-3-methylglutaryl-CoA synthase was not detected. As a result of SDS-PAGE analysis of the crude extract, an expressed protein band that was observed in expressed broth had disappeared. Subsequently, the white pellet that was recovered from the crude lysate of the induced pHMC818 clone was solubilized with 8 M guanidine-HCl, and then subjected to SDS-PAGE analysis. The expressed protein was recovered in the white pellet. This suggested that the expressed protein forms an inclusion body.

Next, an expression experiment in more mild conditions was conducted. Cells were grown in LB medium at 28° C. and the induction was performed by addition of 0.1 mM of IPTG. Subsequently, incubation was continued for another 3.5 hours at 28° C. and then the cells were harvested. Preparation of the crude extract was the same as the previous protocol. Their results are summarized in TABLE 5. It was shown that HMG-CoA synthase activity was only observed in the induced culture of the recombinant strain harboring the hmc gene. This indicates that the cloned hmc gene encodes HMG-CoA synthase.

TABLE 5

Enzymatic characterization of hmc cDNA clone

| plasmid | IPTG | μmol of HMG-CoA/ minute/mg-protein |
|---|---|---|
| PHMC818 | − | 0 |
|  | + | 0.146 |
| PET11c | − | 0 |
|  | + | 0 |

Example 8

Cloning of hmg (3-hydroxymethyl-3-glutaryl-CoA reductase) Gene

In this example, the cloning protocol for the hmg gene was substantially the same as the protocol used to clone the hmc gene shown in Examples 2 to 7. At first, the PCR primers whose sequences are shown in TABLE 6 were synthesized based on the common sequences of HMG-CoA reductase genes from other species.

Table 6

Sequence of Primers Used in the Cloning of hmg Gene

Red1; GCNTGYTGYGARAAYGTNATHGGN-TAYATGCC (sense primer) (SEQ ID NO: 19)
Red2; ATCCARTTDATNGCNGCNGGYTTYTTRTCNGT (antisense primer) (SEQ ID NO: 20)
(N=A, C, G or T; R=A or G; Y=C or T, H=A, T or C, D=A, G or T)

After a PCR reaction of 25 cycles at 95° C. for 30 seconds, 54° C. for 30 seconds and 72° C. for 30 seconds using ExTaq (Takara Shuzo) as a DNA polymerase, the reaction mixture was separated by electrophoresis on an agarose gel. A PCR band that had the desired length was recovered and purified by QIAquick (QIAGEN) according to the manufacturer's method and then ligated into pUC57 vector (MBI Fermentas). After the transformation of competent E. coli DH5α cells with this vector, 7 white colonies were selected and plasmids were isolated from those transformants.

As a result of sequencing, it was found that all the clones had a sequence whose deduced amino acid sequence was similar to known HMG-CoA reductase genes. One of the isolated cDNA clones was designated as pRED 1219 and was used for further study.

Next, a genomic fragment containing 5'- and 3'-regions adjacent to the hmg gene was cloned with the Genome Walker kit (Clontech). The 2.5 kb fragment of 5' adjacent region (pREDPVu1226) and the 4.0 kb fragment of the 3' adjacent region of the hmg gene (pREDEVd1226) were cloned. Based on the sequence of the insert of pREDPVu1226, PCR primers whose sequences are shown in TABLE 7 were synthesized.

Table 7

Sequence of Primers Used in the Cloning of cDNA of hmg Gene

Red8; GGCCATTCCACACTTGATGCTCTGC (antisense primer) (SEQ ID NO: 21)
Red9; GGCCGATATCTTTATGGTCCT (sense primer) (SEQ ID NO: 22)

Subsequently, a cDNA fragment containing a long portion of the hmg cDNA sequence was cloned by PCR using Red 8 and Red 9 as PCR primers and the cDNA pool prepared in Example 2 as template. The cloned plasmid was designated pRED107. The PCR conditions were as follows; 25 cycles for 30 seconds at 94° C., 30 seconds at 55° C. and 1 minute at 72° C.

A Southern blot hybridization study was performed to clone a genomic sequence which contains the entire hmg gene from *P. rhodozyma*. A probe was prepared by labeling a template DNA (pRED107) according to the DIG multipriming method. Hybridization was performed with the method specified by the manufacturer. As a result, the labeled probe hybridized to two bands that were 12 kb and 4 kb in length. As a result of sequencing of pREDPVu1226, an EcoRI site was not found in the cloned hmg region. This suggested that another species of hmg gene (that has 4 kb of hybridized EcoRI fragment) existed on the genome of *P. rhodozyma* as found in other organisms.

Next, a genomic library consisting of 9 to 23 kb of an EcoRI fragment in the λDASHII vector was constructed. The packaged extract was used to infect *E. coli* XL1 Blue, MRA(P2) strain (Stratagene) and over-laid with NZY medium poured onto LB agar medium. About 5000 plaques were screened using the 0.6 kb fragment of StuI-digested pRED107 as a probe. 4 plaques were hybridized to the labeled probe. Then, a phage lysate was prepared and DNA was purified with the Wizard lambda purification system according to the method specified by the manufacturer (Promega). The purified DNA was digested with EcoRI to isolate a 10 kb EcoRI fragment which was cloned into an EcoRI-digested and CIAP-treated pBluescriptII KS- (Stratagene). Eleven white colonies were selected and subjected to a colony PCR using Red9 and −40 universal primer (Pharmacia).

Template DNA for a colony PCR was prepared by heating a cell suspension in which a picked-up colony was suspended in 10 μl of sterilized water for 5 minutes at 99° C. prior to a PCR reaction (PCR conditions; 25 cycles for 30 seconds at 94° C., 30 seconds at 55° C. and 3 minutes at 72° C.). One colony gave 4 kb of a positive PCR band. This indicated that the clone contained the entire hmg gene. A plasmid from this positive clone was prepared and designated pRED611. Subsequently, deletion derivatives of pRED611 were made for sequencing. By combining the sequence obtained from the deletion mutants with the sequence obtained by a primer-walking procedure, the nucleotide sequence of 6370 base pairs which contains the hmg gene from *P. rhodozyma* was determined (SEQ ID NO: 2).

The hmg gene from *P. rhodozyma* consists of 10 exons and 9 introns. The deduced amino acid sequence of 1,091 amino acids in length (SEQ ID NO: 7) showed an extensive homology to known HMG-CoA reductase (53.0% identity to HMG-CoA reductase from *Ustilago maydis*).

Example 9

Expression of Carboxyl-terminal Domain of hmg Gene in *E. coli*

Some species of prokaryotes have soluble HMG-CoA reductases or related proteins (Lam et al., J. Biol. Chem. 267, 5829–5834, 1992). However, in eukaryotes HMG-CoA reductase is tethered to the endoplasmic reticulum via an amino-terminal membrane domain (Skalnik et al., J. Biol. Chem. 263, 6836–6841, 1988). In fungi (i.e., *Saccharomyces cerevisiae* and the smut fungus, *Ustilago maydis*) and in animals, the membrane domain is large and complex, containing seven or eight transmembrane segments (Croxen et al. Microbiol. 140, 2363–2370, 1994). In contrast, the membrane domains of plant HMG-CoA reductase proteins have only one or two transmembrane segments (Nelson et al. Plant Mol. Biol. 25, 401–412, 1994). Despite the difference in the structure and sequence of the transmembrane domain, the amino acid sequences of the catalytic domain are conserved across eukaryotes, archaebacteria and eubacteria.

Croxen et al. showed that the C-terminal domain of HMG-CoA reductase derived from the maize fungal pathogen, *Ustilago maydis* was expressed in active form in *E. coli* (Microbiology, 140, 2363–2370, 1994). The inventors of the present invention tried to express a C-terminal domain of HMG-CoA reductase from *P. rhodozyma* in *E. coli* to confirm its enzymatic activity.

At first, the PCR primers whose sequences were shown in TABLE 8 were synthesized to clone a partial cDNA fragment of the hmg gene. The sense primer sequence corresponds to the sequence which starts from the 597th amino acid (glutamate) residue. The length of the protein and cDNA which was expected to be obtained was 496 amino acids and 1.5 kb, respectively.

Table 8

Sequence of Primers Used in the Cloning of a Partial cDNA of hmg Gene

Red54; GGTACCGAAGAAATTATGAAGAGTGG (sense primer) (SEQ ID NO: 23)
Red55; CTGCAGTCAGGCATCCACGTTCACAC (antisense primer) (SEQ ID NO: 24)

The PCR conditions were as follows; 25 cycles at 95° C. for 30 seconds, 55° C. for 30 seconds and 72° C. for 3 minutes. As a template, 0.1 μg of the cDNA pool obtained in Example 2 and as a DNA polymerase, ExTaq polymerase were used. An amplified 1.5 kb fragment was recovered and cloned in pMOSBlue T-vector (Novagen). Twelve independent clones from white colonies of *E. coli* DH5∇ transformants were selected and plasmids were prepared from those transformants. As a result of restriction analysis, all the clones were selected for further characterization by sequencing. One clone did not have a single amino acid substitution throughout the coding sequence and was designated pRED908.

Next, a 1.5 kb fragment obtained by KpnI- and PstI-digestion of pRED908 was ligated to pQE30 (QIAGEN), digested by the same pairs of restriction enzymes, and transformed to *E. coli* KB822. As a result of the restriction analysis, a plasmid that had a correct structure (pRED1002) was recovered. Then, competent *E. coli* M15 (pREP4) cells (QIAGEN) were transformed and one clone that had a correct structure was selected for further study.

For an expression study, strain M15 (pREP4) (pRED1002) and vector control strain M15 (pREP4) (pQE30) were cultivated in 100 ml of LB medium at 30° C. until the OD at 600 nm reached 0.8 (about 5 hours) in the presence of 25 µg/ml of kanamycin and 100 µg/ml of ampicillin. Then, the broth was divided into two samples of the same volume, and 1 mM of IPTG was added to one sample (induced). Cultivation of both samples continued for another 3.5 hours at 30° C. Twenty five µl of the broth was removed from induced- and uninduced-cultures of the hmg clone and vector control cultures and subjected to SDS-PAGE analysis. It was confirmed that the protein whose size was similar to the deduced molecular weight based on the nucleotide sequence (52.4 kDa) was expressed only in the case of the clone that harbored pRED1002 with the induction.

Cells from 50 ml of broth were harvested by centrifugation (1500×g, 10 minutes), washed once and suspended in 2 ml of hmg buffer (100 mM potassium phosphate buffer (pH 7.0) containing 1 mM of EDTA and 10 mM of dithiothreitol). Cells were disrupted by a French press (Ohtake Works) at 1500 kgf/cm$^2$ to yield a crude lysate. After centrifugation of the crude lysate, a supernatant fraction was recovered and used as a crude extract for enzymatic analysis. Only in the case of the induced lysate of the pRED1002 clone, a white pellet was spun down and recovered. An enzyme assay for 3-hydroxy-3-methylglutaryl-CoA (HMG-CoA) reductase was performed by the photometric assay according to the method by Servouse et al. (Biochem. J. 240, 541–547, 1986). In the crude extract, the activity of 3-hydroxy-3-methylglutaryl-CoA synthase was not detected. As a result of SDS-PAGE analysis for the crude extract, the expressed protein band that was present in the expressed broth was not observed. Next, the white pellet recovered from the crude lysate of induced pRED1002 clone was solubilized with an equal volume of 20% SDS, and then subjected to SDS-PAGE analysis. An expressed protein was recovered in the white pellet, which indicators that the expressed protein would form an inclusion body.

Next, the expression experiment was performed in more mild conditions. Cells were grown in LB medium at 28° C. and the induction was performed by the addition of 0.1 mM of IPTG Then, incubation was continued for another 3.5 hours at 28° C. and then the cells were harvested. Preparation of the crude extract was the same as the previous protocol. Results are summarized in TABLE 9. It was shown that 30 times higher induction was observed, and this suggested that the cloned hmg gene codes HMG-CoA reductase.

TABLE 9

Enzymatic characterization of hmg cDNA clone

| Plasmid | IPTG | µmol of NADPH/ minute/mg-protein |
|---|---|---|
| PRED1002 | − | 0.002 |
| | + | 0.059 |
| pQE30 | − | 0 |
| | + | 0 |

Example 10

Cloning of Mevalonate Kinase (mvk) Gene

The cloning protocol for the mvk gene used in this example was substantially the same as the protocol for the hmc gene shown in Examples 2 to 7. At first, PCR primers whose sequence are shown in TABLE 10, were synthesized based on the common sequences of the mevalonate kinase genes from other species.

Table 10
Sequence of Primers Used in the Cloning of mvk Gene
Mk1; GCNCCNGGNAARGTNATHYTNTTYGGNGA
(sense primer) (SEQ ID NO: 25)
Mk2; CCCCANGTNSWNACNGCRTTRTCNACNCC
(antisense primer) (SEQ ID NO: 26)
(N=A, C, G or T; R=A or G, Y=C or T, H=A, T or C, S=C or G, W=A or T)

After a PCR reaction of 25 cycles at 95° C. for 30 seconds, 46° C. for 30 seconds and 72° C. for 15 seconds using ExTaq as a DNA polymerase, the reaction mixture was separated by electrophoresis on an agarose gel. A 0.6 kb PCR band whose length was expected to contain a partial mvk gene was recovered and purified by QIAquick according to the method indicated by the manufacturer and then ligated to pMOSBlue T-vector. After transformation of competent *E. coli* DH5∀ cells with this construct, 4 white colonies were selected and plasmids were isolated. As a result of sequencing, it was found that one of the clones had a sequence whose deduced amino acid sequence was similar to known mevalonate kinase genes. This cDNA clone was named as pMK128 and was used for further study.

Next, a partial genomic clone which contained the mvk gene was cloned by PCR. The PCR primers whose sequences are shown in TABLE 11, were synthesized based on the internal sequence of pMK128.

Table 11

Sequence of Primers Used in the Cloning of Genomic DNA Containing mvk Gene

Mk5; ACATGCTGTAGTCCATG (sense primer) (SEQ ID NO: 27)
Mk6; ACTCGGATTCCATGGA (antisense primer) (SEQ ID NO: 28)

The PCR conditions were 25 cycles for 30 seconds at 94° C., 30 seconds at 55° C. and 1 minute at 72° C. The amplified 1.4 kb fragment was cloned into pMOSBlue T-vector. As a result of sequencing, it was confirmed that a genomic fragment containing the mvk gene which had typical intron structures could be obtained and this genomic clone was designated pMK224.

A Southern blot hybridization study was performed to clone a genomic fragment which contained an entire mvk gene from *P. rhodozyma*. A probe was prepared by labeling a template DNA, pMK224 digested by NcoI with the DIG multipriming method. Hybridization was performed with the method specified by the manufacturer. As a result, the labeled probe hybridized to a 6.5 kb band.

Next, a genomic library consisting of a 5 to 7 kb EcoRI fragment was constructed in the 8ZAPII vector. The packaged extract was used to infect *E coli* XL1Blue, MRF' strain (Stratagene) and over-laid with NZY medium poured onto LB agar medium. About 5000 plaques were screened using a 0.8 kb NcoI-fragment digested from pMK224 as a probe. Seven plaques were hybridized to the labeled probe. Then a phage lysate was prepared according to the method specified by the manufacturer (Stratagene) and in vivo excision was performed using *E. coli* XL1Blue MRF' and SOLR strains. Fourteen white colonies were selected and plasmids were isolated from those selected transformants. Then, isolated plasmids were digested by NcoI and subjected to Southern blot hybridization with the same probe as the plaque hybridization. The insert fragments of all the plasmids hybridized to the probe. This indicated that a genomic fragment containing the mvk gene could be cloned. A plasmid from one of the positive clones was prepared and designated as pMK701. About 3 kb of sequence was determined by the primer walking procedure and it was revealed that the 5' end of the mvk gene was not contained in pMK701.

Next, a PCR primer was synthesized which had the following sequence;
TTGTTGTCGTAGCAGTGGGTGAGAG (SEQ ID NO: 29).

This primer was used to clone the 5'-adjacent genomic region of the mvk gene with the Genome Walker Kit according to the method specified by the manufacturer (Clontech). A specific 1.4 kb PCR band was amplified and cloned into pMOSBlue T-vector. All of the transformants of DH5∀ selected had the expected length of the insert. Subsequent sequencing revealed that the 5'-adjacent region of the mvk gene could be cloned. One of the clones was designated as pMKEVR715 and was used for further study. As a result of Southern blot hybridization using the genomic DNA prepared in example 3, the labeled pMKEVR715 construct hybridized to a 2.7 kb EcoRI band. Then, a genomic library in which EcoRI fragments from 1.4 to 3.0 kb in length were cloned into 8ZAPII was constructed. This genomic library was screened with a 1.0 kb EcoRI fragment from pMKEVR715. Fourteen positive plaques were selected from 5000 plaques and plasmids were prepared from those plaques with the in vivo excision procedure.

The PCR primers whose sequences are shown in TABLE 12, taken from the internal sequence of pMKEVR715 were synthesized to select a positive clone with a colony PCR.

Table 12

PCR Primers Used for Colony PCR to Clone 5'-adjacent Region of mvk Gene

Mk17; GGAAGAGGAAGAGAAAAG (sense primer) (SEQ ID NO: 30)
Mk18; TTGCCGAACTCAATGTAG (antisense primer) (SEQ ID NO: 31)

PCR conditions were as follows: 25 cycles for 30 seconds at 94° C., 30 seconds at 50° C. and 15 seconds at 72° C. From all the candidates except one clone, the positive 0.5 kb band was yielded. One of the clones was selected and designated pMK723 to determine the sequence of the upstream region of mvk gene. After sequencing the 3'-region of pMK723 and combining it with the sequence of pMK701, the genomic sequence of the 4.8 kb fragment containing the mvk gene was determined.

The mvk gene consists of 4 introns and 5 exons (SEQ ID NO: 3). The deduced amino acid sequence except 4 amino acids at the amino terminal end (SEQ ID NO: 8) showed an extensive homology to known mevalonate kinase (44.3% identity to mevalonate kinase from *Rattus norvegicus*).

Example 11

Expression of mvk Gene by the Introduction of 1 Base at the Amino Terminal Region Although the amino acid sequence showed a significant homology to known mevalonate kinase, an appropriate start codon for mvk gene could not be found. This result indicated that the cloned gene might be a pseudogene for mevalonate kinase. To confirm this assumption, PCR primers whose sequences are shown in TABLE 13 were synthesized to introduce an artificial nucleotide which resulted in the generation of an appropriate start codon at the amino terminal end.

Table 13

PCR Primers Used for the Introduction of a Nucleotide into mvk Gene

Mk33; GGATCCATGAGAGCCCAAAAAGAAGA (sense primer) (SEQ ID NO: 32)
Mk34; GTCGACTCAAGCAAAAGACCAACGAC (antisense primer) (SEQ ID NO: 33)

The artificial amino terminal sequence thus introduced was as follows; NH2-Met-Arg-Ala-Gln. After the PCR reaction of 25 cycles at 95° C. for 30 seconds, 55° C. for 30 seconds and 72° C. for 30 seconds using ExTaq polymerase as a DNA polymerase, the reaction mixture was subjected to agarose gel electrophoresis. An expected 1.4 kb PCR band was amplified and cloned into the pCR2.1 TOPO vector. After transformation of competent *E. coli* TOP10 cells, 6 white colonies were selected and plasmids were isolated. As a result of sequencing, it was found that one clone had only one amino acid residue change (Asp to Gly change at 81st amino acid residue in SEQ ID NO: 8). This plasmid was named pMK1130 #3334 and used for further study.

Then, the insert fragment of pMK1130 #3334 was cloned into pQE30. This plasmid was named pMK1209 #3334. After transformation of the expression host, M15 (pREP4), an expression study was conducted. The M15 (pREP4) (pMK1209 #3334) strain and vector control strain (M15 (pREP4) (pQE30)) were inoculated into 3 ml of LB medium containing 100 μg/ml of ampicillin. After cultivation at 37° C. for 3.75 hours, the culture broth was divided into two samples. 1 mM IPTG was added to one sample (induced) and incubation of all samples was continued for 3 hours. Cells were harvested from 50 μl of broth by centrifugation and were subjected to SDS-PAGE analysis. A protein which had an expected molecular weight of 48.5 kDa was induced by the addition of IPTG in the culture of M15 (pREP4) (pMK1209 #3334) although no induced protein band was observed in the vector control culture (FIG. 2). This result suggested that the activated form of the mevalonate kinase protein could be expressed by artificial addition of one nucleotide at the amino terminal end.

Example 12

Cloning of the Mevalonate Pyrophosphate Decarboxylase (mpd) Gene

In this example, the cloning protocol for the mpd gene was substantially the same as used to clone the hmc gene shown in Examples 2 to 7. At first, the PCR primers whose sequences are shown in TABLE 14 were synthesized based on the common sequences of the mevalonate pyrophosphate decarboxylase gene from other species.

Table 14

Sequence of Primers Used in the Cloning of the mpd Gene

Mpd1; HTNAARTAYTTGGGNAARMGNGA (sense primer) (SEQ ID NO: 34)
Mpd2; GCRTTNGGNCCNGCRTCRAANGTRTANGC (antisense primer) (SEQ ID NO: 35)
(N=A, C, G or T; R=A or G, Y=C or T, H=A, T or C, M=A or C)

After the PCR reaction of 25 cycles at 95° C. for 30 seconds, 50° C. for 30 seconds and 72° C. for 15 seconds using ExTaq as a DNA polymerase, the reaction mixture was subjected to agarose gel electrophoresis. A 0.9 kb PCR band whose length was expected to contain a partial mpd gene was recovered and purified by QIAquick according to the method prepared by the manufacturer and then ligated to pMOSBlue T-vector. After transformation of competent E. coli DH5∇ cells, 6 white colonies were selected and plasmids were isolated therefrom. Two of the 6 clones had the expected insert length. As a result of sequencing, it was found that one of the clones had a sequence whose deduced amino acid sequence was similar to known mevalonate pyrophosphate decarboxylase genes. This cDNA clone was designated pMPD129 and was used for further study.

Next, a partial genomic fragment which contained the mpd gene was cloned by PCR. As a result of PCR (whose condition was the same as that of the cloning of a partial cDNA fragment), the amplified 1.05 kb fragment was obtained and was cloned into pMOSBlue T-vector. As a result of sequencing, it was confirmed that a genomic fragment containing the mpd gene which had typical intron structures had been obtained. This genomic clone was designated pMPD220.

A Southern blot hybridization study was performed to clone a genomic fragment which contained the entire mpd gene from P. rhodozyma. The probe was prepared by labeling a template DNA, pMPD220 digested by KpnI, using the DIG multipriming method. Hybridization was performed using the method specified by the manufacturer. As a result, the probe hybridized to a band that was 7.5 kb in length. Next, a genomic library containing a 6.5 to 9.0 kb EcoRI fragment in the δZAPII vector was constructed. The packaged extract was used to infect an E. coli XL1Blue, MRF' strain and was over-laid with NZY medium poured onto LB agar medium. About 6000 plaques were screened using the 0.6 kb fragment of KpnI-digested pMPD220 as a probe. 4 plaques were hybridized to the labeled probe. Then, a phage lysate was prepared according to the method specified by the manufacturer (Stratagene) and an in vivo excision was performed using E. coli XL1Blue MRF' and SOLR strains. 3 white colonies derived from 4 positive plaques were selected and plasmids were isolated from those selected transformants. Then, the isolated plasmids were subjected to a colony PCR method whose protocol was the same as that in example 8. PCR primers whose sequences are shown in TABLE 14, depending on the sequence found in pMPD129 were synthesized and used for a colony PCR.

Table 15

Sequence of Primers Used in the Colony PCR to Clone a Genomic mpd Clone

Mpd7; CCGAACTCTCGCTCATCGCC (sense primer) (SEQ ID NO: 36)

Mpd8; CAGATCAGCGCGTGGAGTGA (antisense primer) (SEQ ID NO: 37)

The PCR conditions were substantially the same as used in the cloning of the mvk gene; 25 cycles for 30 seconds at 94° C., 30 seconds at 50° C. and 10 seconds at 72° C. All the clones, except one, produced a positive 0.2 kb PCR band. A plasmid was prepared from one of the positive clones and the plasmid was designated pMPD701 and about 3 kb of its sequence was determined by the primer walking procedure (SEQ ID NO: 4). The ORF consisted of 401 amino acids (SEQ ID NO: 9) whose sequence was similar to the sequences of known mevalonate pyrophosphate decarboxylase (52.3% identity to mevalonate pyrophosphate decarboxylase from Schizosaccaromyces pombe). Also determined was a 0.4 kb fragment from the 5'-adjacent region which was expected to include its promoter sequence.

Example 13

Cloning of Farnesyl Pyrophosphate Synthase (fps) Gene

In this example, the cloning protocol for the fps gene was substantially the same as the protocol for cloning the hmc gene shown in Examples 2 to 7. At first, the PCR primers whose sequences are shown in TABLE 16 were synthesized based on the common sequences of the farnesyl pyrophosphate synthase gene from other species.

Table 16

Sequence of Primers Used in the Cloning of fps Gene

Fps1; CARGCNTAYTTYYTNGTNGCNGAYGA (sense primer) (SEQ ID NO: 38)
Fps2; CAYTTRTTRTCYTGDATRTCNGTNCCDATYTT (antisense primer) (SEQ ID NO: 39)
(N=A, C, G or T; R=A or G, Y=C or T, D=A, G or T)

After the PCR reaction of 25 cycles at 95° C. for 30 seconds, 54° C. for 30 seconds and 72° C. for 30 seconds using ExTaq as a DNA polymerase, the reaction mixture was subjected to agarose gel electrophoresis. A PCR band that had the desired length (0.5 kb) was recovered and purified by QIAquick according to the method prepared by the manufacturer and then ligated to pUC57 vector. After transformation of competent E. coli DH5∇ cells, 6 white colonies were selected and plasmids were then isolated. One of the plasmids which had the desired length of an insert fragment was sequenced. As a result, it was found that this clone had a sequence whose deduced amino acid sequence was similar to known farnesyl pyrophosphate synthase genes. This cDNA clone was named as pFPS107 and was used for further study.

Next, a genomic fragment was cloned by PCR using the same primer set of Fps1 and Fps2. The same PCR conditions for the cloning of a partial cDNA were used. A 1.0 kb band was obtained which was subsequently cloned and sequenced. This clone contained the same sequence as the pFPS107 and some typical intron fragments. This plasmid was designated pFPS113 and was used for a further experiment.

Then, a 5'- and 3'-adjacent region containing the fps gene was cloned according to the method described in Example 8. At first, the PCR primers whose sequences are shown in TABLE 17 were synthesized.

Table 17

Sequences of Primers Used for a Cloning of Adjacent Region of fps Gene

Fps7; ATCCTCATCCCGATGGGTGAATACT (sense for downstream cloning) (SEQ ID NO: 40)

Fps9; AGGAGCGGTCAACAGATCGATGAGC (antisense for upstream cloning) (SEQ ID NO: 41)

Amplified PCR bands were isolated and cloned into pMOSBlue T-vector. As a result of sequencing, it was found that the 5'-adjacent region (2.5 kb in length) and the 3'-adjacent region (2.0 kb in length) were cloned. These plasmids were designated pFPSSTu117 and pFPSSTd117, respectively. After sequencing both plasmids, an ORF was found that consisted of 1068 base pairs with 8 introns. The deduced amino acid sequence showed an extensive homology to known farnesyl pyrophosphate synthase from other species. Based on the sequence determined, two PCR primers were synthesized with the sequences shown in TABLE 17 to clone a genomic fps clone and a cDNA clone for fps gene expression in *E. coli*.

Table 18

Sequences of Primers Used for a cDNA and Genomic fps Cloning

Fps27; GAATTCATATGTCCACTACGCCTGA (sense primer) (SEQ ID NO: 42)
Fps28; GTCGACGGTACCTATCACTCCCGCC (antisense primer) (SEQ ID NO: 43)

The PCR conditions were as follows; 25 cycles for 30 seconds at 94° C., 30 seconds at 50° C. and 30 seconds at 72° C. One cDNA clone that had the correct sequence was selected as a result of sequencing analysis of the clones obtained by PCR and was designated pFPS113. Next, a Southern blot hybridization study was performed to clone a genomic fragment which contained the entire fps gene from *P. rhodozyma*. The probe was prepared by labeling a template DNA, pFPS113 using the DIG multipriming method. As a result, the labeled probe hybridized to a band that was about 10 kb.

Next, a genomic library consisting of 9 to 15 kb of an EcoRI fragment was constructed in a 8DASHII vector. The packaged extract was used to infect *E. coli* XL1 Blue, MRA(P2) strain (Stratagene) and over-laid with NZY medium poured onto LB agar medium. About 10000 plaques were screened using the 0.6 kb fragment of SacI- digested pFPS113 as a probe. Eight plaques were hybridized to the labeled probe. Then, a phage lysate was prepared according to the method specified by the manufacturer (Promega). All the plaques were subjected to a plaque PCR using Fps27 and Fps28 primers.

Template DNA for a plaque PCR was prepared by heating 2 μl of a solution of phage particles for 5 minutes at 99° C. prior to the PCR reaction. The PCR conditions were the same as that of the pFPS113 cloning hereinbefore. All the plaques gave a 2 kb positive PCR band. This suggested that these clones had an entire region containing the fps gene. One of the 8DNAs that harbored the fps gene was digested with EcoRI to isolate a 10 kb EcoRI fragment which was cloned into an EcoRI-digested and CIAP-treated pBluescriptII KS- (Stratagene).

Twelve white colonies from transformed *E. coli* DH5∀ cells were selected and plasmids were prepared from these clones and subjected to colony PCR using the same primer sets of Fps27 and Fps28 and the same PCR conditions. A 2 kb positive band was yielded from 3 of 12 candidates. One clone was cloned and designated pFPS603. It was confirmed that the sequence of the fps gene which was previously determined from the sequence of pFPSSTu117 and pFPSStd117 was substantially correct although there were some PCR errors. Finally, the nucleotide sequence was determined of the 4,092 base pairs which contains the fps gene from *P. rhodozyma* (FIG. 3). An ORF which consisted of 355 amino acids with 8 introns was found (SEQ ID NO: 5). The deduced amino acid sequence (SEQ ID NO: 10) showed an extensive homology to known FPP synthase (65% identity to FPP synthase from *Kluyveromyces lactis*).

The invention being thus described, it will be seen that the same may be varied in many ways. Such variations are not to be regarded as a departure from the spirit and scope of the invention and all such modifications are intended to be included within the scope of the following claims.

What is claimed is:

1. An isolated DNA sequence comprising a DNA sequence that hybridizes to SEQ ID NO:2 under the following conditions: hybridization in 50% formnamide (v/v), 2% blocking agent, 5×SSC, 0.1% N-lauroylsarcosine (w/v), and 0.1% SDS at 42° C. overnight followed by two washes for 5 minutes each in 2×SSC and 0.1% SDS at room temperature followed by two additional washes of 15 minutes each in 0.1×SSC and 0.1% SDS at 68° C., wherein the DNA sequence encodes an amino acid sequence having 3-hydroxy-3-methylglutaryl-CoA reductase (HMG-CoA reductase) activity.

2. An isolated DNA sequence according to claim 1 wherein the DNA sequence encodes the amino acid sequence set forth in SEQ ID NO:7.

3. An isolated DNA sequence according to claim 1 comprising SEQ ID NO:2.

4. An isolated DNA sequence according to claim 3 consisting essentially of SEQ D NO:2.

5. An isolated DNA sequence according to claim 1 consisting of SEQ ID NO:2 or a fragment thereof, which fragment encodes an amino acid sequence having HMG-CoA reductase activity.

6. An isolated DNA sequence according to claim 1 wherein the DNA sequence is an isocoding variant of the DNA sequence of SEQ ID NO:2.

7. An isolated DNA sequence according to claim 1 wherein the DNA sequence that hybridizes to SEQ D NO:2 is a derivative of SEQ ID NO:2, which contains an addition, insertion, deletion, and/or substitution of one or more nucleotide(s).

8. An isolated DNA sequence according claim 1 wherein the DNA sequence is derived from a *Phaffia rhodozyma* gene and is selected from the group consisting of SEQ ID NO:2, an isocoding variant of SEQ ID NO:2, and a derivative of a SEQ ID NO:2 having an addition, insertion, deletion and/or substitution of one or more nucleotide(s).

9. A vector or plasmid comprising a DNA sequence according to claim 1.

10. A host cell transformed or transfected with a DNA sequence according to claim 1.

11. A host cell transformed or transfected with a vector or plasmid according to claim 9.

12. A process for producing an enzyme for converting acetyl Co-A to isopentyl pyrophosphate, which enzyme is in the mevalonate biosynthetic pathway or for converting isopentyl pyrophosphate to farnesyl pyrophosphate, which comprises culturing a host ing to claim 10, under conditions wherein the enzyme is produced.

13. A process for the production of isoprenoids or carotenoids, which growing a host cell according to clam 10 under conditions wherein isoprenoids or carotenoids are produced.

14. A process according to claim 13 wherein the carotenoid is astaxanthin.

15. An isolated DNA sequence comprising a DNA sequence that does not to SEQ ID NO:2 but which encodes an amino acid sequence that is identical to SEQ ID NO:7.

* * * * *

UNITED STATES PATENT AND TRADEMARK OFFICE
CERTIFICATE OF CORRECTION

PATENT NO.    : 6,284,506 B1
DATED         : September 4, 2001
INVENTOR(S)   : Tatsuo Hoshino et al.

It is certified that error appears in the above-identified patent and that said Letters Patent is hereby corrected as shown below:

Title page,
Under Item [75] Inventors, please change "Kamakura" to -- Kamakura-shi --, and "Fujisawa" to -- Fujisawa-shi --;
Under Item [56] References Cited, in front of "10-248575" please add -- JP --;

Column 77,
Line 27, please change "SEQ D NO:2" to -- SEQ ID NO:2 --;

Column 78,
Line 1, after "according" please add -- to --;
Line 18, please change "host ing" to -- host cell according --;
Line 21, after "which" please insert -- comprises --;
Line 27, after "not" please insert -- hybridize --.

Signed and Sealed this

Fifth Day of March, 2002

Attest:

Attesting Officer

JAMES E. ROGAN
Director of the United States Patent and Trademark Office

SEQUENCE LISTING

```
<160> NUMBER OF SEQ ID NOS: 43

<210> SEQ ID NO 1
<211> LENGTH: 4775
<212> TYPE: DNA
<213> ORGANISM: Phaffia rhodozyma
<220> FEATURE:
<221> NAME/KEY: 5'UTR
<222> LOCATION: (1239)..(1240)
<223> OTHER INFORMATION: EXPERIMENTAL
<221> NAME/KEY: exon
<222> LOCATION: (1305)..(1361)
<221> NAME/KEY: intron
<222> LOCATION: (1362)..(1504)
<221> NAME/KEY: exon
<222> LOCATION: (1505)..(1522)
<221> NAME/KEY: intron
<222> LOCATION: (1523)..(1699)
<221> NAME/KEY: exon
<222> LOCATION: (1700)..(1826)
<221> NAME/KEY: intron
<222> LOCATION: (1827)..(1920)
<221> NAME/KEY: exon
<222> LOCATION: (1921)..(2277)
<221> NAME/KEY: intron
<222> LOCATION: (2278)..(2351)
```

```
<221> NAME/KEY: exon
<222> LOCATION: (2352)..(2409)
<221> NAME/KEY: intron
<222> LOCATION: (2410)..(2497)
<221> NAME/KEY: exon
<222> LOCATION: (2498)..(2504)
<221> NAME/KEY: intron
<222> LOCATION: (2505)..(2586)
<221> NAME/KEY: exon
<222> LOCATION: (2587)..(2768)
<221> NAME/KEY: intron
<222> LOCATION: (2769)..(2851)
<221> NAME/KEY: exon
<222> LOCATION: (2852)..(2891)
<221> NAME/KEY: intron
<222> LOCATION: (2892)..(2985)
<221> NAME/KEY: exon
<222> LOCATION: (2986)..(3240)
<221> NAME/KEY: intron
<222> LOCATION: (3241)..(3325)
<221> NAME/KEY: exon
<222> LOCATION: (3326)..(3493)
<221> NAME/KEY: intron
<222> LOCATION: (3494)..(3601)
<221> NAME/KEY: exon
<222> LOCATION: (3602)..(3768)
<221> NAME/KEY: polyA_site
<222> LOCATION: (4043)..(4044)

<400> SEQUENCE: 1
catcgaagag agcgaagtga ttagggaagc cgaagaggca ctaacaacgt ggttgtatat    60
gtgtgtttat gagtgttata tcgtcaagaa cgaagtccat tcatttagct agacagggag   120
agagggagaa acgtacgggt ttaccctatt ggaccagtct aaagagagaa cgagagtttt   180
tgggtcggtc acctgaagag tttgaacctc cacaagttta ttctagatta tttccggggg   240
tatgtgaagg ataatgtcaa actttgtcca gattgaagaa ggcaagaaag gaaaggggcg   300
aacgagagta tcgtcccatc tatgggtgac cagtcgacct tctgcatcgg cgatcccgag   360
aatggaaggt tccgatggat cagaagtagg tttcctaagc tcaaacatag gtcattgcga   420
gtgagataca tatgcagact gatatgctag tcaaaccgaa cgagatttct ctgtttgctt   480
tcaaaaagac gaaccaacca tttcatgtcc aagatggcag gtccttcgat tctttgaagc   540
tcctccctga tgcggacaga aaagaataaa aagtagacag actgtcaagt cgacagcgca   600
agtttatcaa gctgagcgag aaaactcgaa cttacatacc ttggccgtca gttctgtaga   660
ccaagcatcg gccttttcctc tttgcggcag gtgtacgcgt tggctcacca tcgtcactct   720
cgtctcctga cccgttgctt tccttgacag cagtctgttc cacaggtttc tctaactgat   780
aggtcccaac agcaaagata tctggatgtc tatgtgagaa ctctactgag tcggcagagt   840
acaccgtatc gatataggcg agtgaggaag ctttgaaagg tgaagaagta gcgaaagatc   900
atcagcgaat gaggactatg acaaaaaaga aattttcgta taatccactg gacaaatcac   960
cttccatcgt gtcctccaag agggtttcgt ctgaaacgta aggacgaggt attgatagat  1020
gattgacctt gagtacgcgg atggacaagg aacgagccca ctcccagggc tatgtaacac  1080
cacacgtgac tccacttgaa ttgcggcaga taaacgaagt cttacgatcg gacgactttg  1140
taaccattta gttatttacc cgtcttgttt tcttactttg atcgtcccat tttagacaca  1200 aaaaagaag ccagaagaga aaagaataaa acgtctaccg tgttctctcc gaattcttac  1260
cacacccaca aaaccataca caatctcaat ctagatatcc agttatgtac acttctacta  1320
ccgaacagcg acccaaagat gttggaattc tcggtatgga ggtatgttgt tcaattctgt  1380
ttgtgttcaa tctttaatca tctttagtcg actgaccggt tcttccttttt ttttttctca  1440
```

```
tcaaacaaaa caacccttct cgattcatgt catctttctt tccaatgcgc tactccttct    1500
gtagatctac tttcctcgac gagtgcgtaa ctattctctc ttctgcattc tctctctatt    1560
cccatgttcg atccctcgcc ctcatatggg cgactgtttc atctcttttg cttccgtcca    1620
ttcttctttg atcttgttca ttttctacta atatctcccg acgcgaaata caacactgac    1680
cgcgatttct ctcgatcagg ccatcgctca caaggatctc gaggcttttg atggggttcc    1740
ttccggaaag tacaccatcg gtctcggcaa caacttcatg gccttcaccg acgacactga    1800
ggacatcaac tcgttcgcct tgaacggtca gtctcttccg tttcagcaat cgacaggaaa    1860
aaggcccaag cgcatctcac tgacaccttt ctccgttttg caattccatt tgattgttag    1920
ctgtttccgg tcttctatca agtacaacg ttgatcccaa gtcaatcggt cgaattgatg    1980
tcggaactga gtccatcatt gacaagtcca aatctgtcaa gacagtcctt atggacttgt    2040
tcgagtccca cggcaacaca gatattgagg gtatcgactc caagaatgcc tgctacggtt    2100
ctaccgcggc cctgttcaat gccgtcaact ggatcgagtc atcctcttgg gacggaagaa    2160
atgccattgt cttctgcgga gacattgcca tctacgccga gggtgctgcc cgacctgccg    2220
gaggtgctgg tgcttgcgcc atcctcatcg gacccgacgc tcccgtcgtc ttcgagcgtg    2280
agttccaatc cgtcattttc ttccacggca gcggctgaaa caaccccttat ccgtcattct    2340 catcaatcta gccgtccacg gaaacttcat gaccaacgct tgggacttct acaagcctaa    2400 tcttcttcg tatgttcaaa ttttgaagtt tgcgcttggg agagtcttac actaattcgg    2460
ggtgctcgta tccttcgaat cgtttgttgc tttatagtga atacgttcgt ctgcgcacct    2520
cctatattta gttttgatc aaatattgtc cattgaatta actctgaaac cttctcctcc    2580
aaatagccca ttgtcgatgg acctctctcc gtcacttcct acgtcaacgc cattgacaag    2640
gcctatgaag cttaccgaac aaagtatgcc aagcgatttg gaggacccaa gactaacggt    2700
gtcaccaacg gacacaccga ggttgccggt gtcagtgctg cgtcgttcga ttaccttttg    2760
ttccacaggt aagcgtcatc ttctgtattc tccttaaatt caaccgatca acggagttaa    2820
ttcgtgtcat catattatct tgttggaaca gtccttacgg aaagcaggtt gtcaaaggcc    2880
acggccgact tgtaagcagt ctttttgtaa ctcttagctt gcagataaaa acttttaggt    2940
ttctggtact cattatttat gcatctcttg aatcacctta tctagttgta caatgacttc    3000
cgaaacaacc ccaacgaccc ggttttgct gaggtgccag ccgagcttgc tactttggac    3060
atgaagaaaa gtctttcaga caagaatgtc gagaaatctc tgattgctgc ctccaagtct    3120
tctttcaaca agcaggttga gcctggaatg accaccgtcc gacagctcgg aaacttgtac    3180
accgcctctc tcttcggtgc tctcgcaagt ttgttctcta atgttcctgg tgacgagctc    3240
gtaagtcttg atctctatcc caatcatctc ttccttatca attgaactga actcttttct    3300
ttaatgctgg ctttctcttg aacaggtcgg caagcgcatt gctctctacg cctacggatc    3360
tggagctgct gcttctttct atgctcttaa ggtcaagagc tcaaccgctt tcatctctga    3420
gaagcttgat ctcaacaacc gattgagcaa catgaagatt gtccctgtg atgactttgt    3480 caaagctctg aaggtacgtt ggataatgac ttttttttgtg gaccgtggtc tttgtcaacc    3540
gctaacaacc ttcttgaatc ggtctctttt ggtttgaaat tcgctcggcg cttcgacaca    3600
ggtccgagaa gagactcaca acgccgtgtc atattcgccc atcggttcgc ttgacgatct    3660
ctggcctgga tcgtactact tgggagagat tgacagcatg tggcgtcgac agtacaagca    3720
ggtcccttct gcttgaacgg gatattaaaa gtttcaaaag ttatgaaaga ggtcggcgaa    3780
gattcaaaat aaataaatat aacaccttgc ttttggctt gttttccttc ttcactctcg    3840
```

```
tttccgatgt gtttcctccg tttcttccct cttttgttcc ttttcctcc ctcttttggt    3900 tacaatctct ttgggtttta caggctggca atctctgtac aatcttcgtt cgcgtgatcc    3960
gacatagata ccgttgtggc atacaccttg cgtcttacat cttttgagag cttcggaggt    4020
gatcttgatg aagaaaattc accattgact cccatctctt gaatgtcctg actaaattga    4080
attggaagca acttatatga agagcaaatt gatggatcca gaaaggaaca agtctagaaa    4140
tcagtgattt gtgcgaaaaa tcagcaaatg ccgcgctgag ccgctcgctg gggagtagac    4200
attgcccatg cgcgtgatgt tgtctgaccg ttctcctcca ttcccccact ctcaaccttc    4260
ctctctttga gaatcgaaga agaaggcgaa gaaaacctga cttgatcctt tacagggtgt    4320
ttcttttgtt cgtatctgag ttactttttcc tcctttcctt cctgcttgag tgaatgactg    4380
atctgactcc tccgcctacc tcggcgactg ggctatatct tgaggataga atatccccct    4440
gacaatccca tttctcaaga ttctttcaaa caagaaaact agttccaatc aatagatcat    4500
ctgatcaacc ttgtgtgaac ataatcatct gcagaagcac tgaactgaga agtcttcct     4560 cagaggaaag agaatactag ataagatcat tcggttggga aggtaaagga atgaagtctg    4620
gttctgggtt tagctctggt tccgtagggg gttcgactat agtttcttct gttcgactag    4680
aaacaggaga aaccgtacat gtaaatggta tgatattctt gtctctgtat catgtcccgc    4740
tcatctcttt gtttgcaagt cactctggag aattc                               4775
```

<210> SEQ ID NO 2
<211> LENGTH: 6370
<212> TYPE: DNA
<213> ORGANISM: Phaffia rhodozyma
<220> FEATURE:
<221> NAME/KEY: 5'UTR
<222> LOCATION: (1043)..(1044)
<223> OTHER INFORMATION: EXPERIMENTAL
<221> NAME/KEY: exon
<222> LOCATION: (1441)..(1446)
<221> NAME/KEY: intron
<222> LOCATION: (1467)..(1722)
<221> NAME/KEY: exon
<222> LOCATION: (1723)..(1813)
<221> NAME/KEY: intron
<222> LOCATION: (1814)..(1914)
<221> NAME/KEY: exon
<222> LOCATION: (1915)..(2535)
<221> NAME/KEY: intron
<222> LOCATION: (2536)..(2621)
<221> NAME/KEY: exon
<222> LOCATION: (2622)..(2867)
<221> NAME/KEY: intron
<222> LOCATION: (2868)..(2942)
<221> NAME/KEY: exon
<222> LOCATION: (2943)..(3897)
<221> NAME/KEY: intron
<222> LOCATION: (3898)..(4030)
<221> NAME/KEY: exon
<222> LOCATION: (4031)..(4516)
<221> NAME/KEY: intron
<222> LOCATION: (4517)..(4616)
<221> NAME/KEY: exon
<222> LOCATION: (4617)..(4909)
<221> NAME/KEY: intron
<222> LOCATION: (4910)..(5007)
<221> NAME/KEY: exon
<222> LOCATION: (5008)..(5081)
<221> NAME/KEY: intron
<222> LOCATION: (5082)..(5195)
<221> NAME/KEY: exon
<222> LOCATION: (5196)..(5446)
<221> NAME/KEY: intron
<222> LOCATION: (5447)..(5523)
<221> NAME/KEY: exon
<222> LOCATION: (5524)..(5756)
<221> NAME/KEY: polyA_site
<222> LOCATION: (6173)..(6174)

<400> SEQUENCE: 2

| | | | | | |
|---|---|---|---|---|---|
| ggaagacatg | atggtgtggg | tgtgagtatg | agcgtgagcg | tgggtatggg | cctgggtgtg | 60 |
| ggtatgagcg | gtggtggtga | tggatggatg | ggtgggtggc | gtggaggggt | ccgtgcggca | 120 |
| agatgttttc | tctgggtagg | agcgttctgc | attggggcag | gagaaaaaat | agtgtggtta | 180 |
| cgggagatcg | tggttacatc | aagccatcgt | cactgtaagg | ctctgtaagg | ctcggttgtt | 240 |
| aagaaggtaa | ccaagtgtaa | tcacttggtt | cgcggggtga | cacttaggct | ctggcgatta | 300 |
| atatatctga | agcagaccaa | actattaaca | atatactttt | ggataagagg | tttcaacaag | 360 |
| aatctcagct | tgaggaaaac | tcttatccaa | gaaggcgcga | gggcgtcccc | gttttatatc | 420 |
| aggacccctc | gcgcatttgg | tctgccacta | aagatataca | tatgacgagc | ctagagaggc | 480 |
| tcgagatcac | gaaaactaaa | aagatgaagc | atgaaccatg | caaactagag | catgatggaa | 540 |
| aatgggcgaa | gaggcataag | ggatggaggg | aacgaatagc | ctgtagggt | aacccacgta | 600 |
| agagaacacg | tgatacttaa | cccgtatccc | tgacagtcac | ggtgtttctt | gagagtcagt | 660 |
| aatgtccagc | tgtgacctca | cgtgactaaa | cccgacacgt | gtgcttcgac | cgaggtggga | 720 |
| cgatcttttt | tttggggga | gaaaccgagt | gggacgatag | agaggactac | ggagaactgt | 780 |
| agtgaattgt | agtgcgctca | ctacggagag | ttctagttga | gcaagcgatg | tgattttcaa | 840 |
| tacaatcccg | gactacaagc | tctctaatag | agctctataa | tagaaggaca | aaagtcgtcc | 900 |
| cactcctatc | tcccgcgcgt | tttaatagag | accgattgtt | ttttcccta | atgttttatt | 960 |
| ttctttcccc | gatcggctca | ttttttcttct | ctccgcgtat | tcttcacaca | acgctccctc | 1020 |
| cgatcttttt | tcttcttgtt | cctgttcctc | ttcgtctcct | tccattgtct | tctttccttc | 1080 |
| cttccttcct | tcttgcctct | agccagcttc | aacagcgacg | tctctctctc | tctgtgtggt | 1140 |
| gatctccgac | tgtagtgtct | ctctcggtca | cttttcacgaa | tcaacttcgt | ttcttttctg | 1200 |
| atcgatcggt | cgtctttccc | tcaatccgtg | catacactca | cacttacact | cacacccaca | 1260 |
| cactcaaaca | cgctaaataa | tcagatccgt | ctccccttct | tgatctcctt | cggcttaggc | 1320 |
| aatggcttcc | ttgttcggcc | tccggcggtc | ctcaaacgag | cagccgcgct | ctcctctgct | 1380 |
| catccaatcg | aagtcatcct | ttctacctt | gtcgtggtca | ccttgacgta | ctttcagttg | 1440 |
| atgtacacca | tcaagcacag | taatttgtac | gtccgatcat | ctatttgtcg | tgttctcctt | 1500 |
| agtctctttc | tcttcctcct | ttgtctttcg | cgtcagcgtg | gctggatttc | cgtctccatg | 1560 |
| tcatttccct | tatttcctct | tcctgtcatt | tgttcctcta | cttttctttc | tctacctcct | 1620 |
| ttccctgtcg | tttgctttcc | ttcgccagtt | gaccaccgat | cctcaggatt | catggctaac | 1680 |
| atgcccaaca | caaacttgca | tatcatctct | cttcgtccac | agtctttctc | agacgattag | 1740 |
| cacacaatct | accaccagct | gggtcgtcga | tgcgttcttc | tctttgggat | ccagatacct | 1800 |
| tgacctcgcg | aaggttagtc | agttgaccct | ctcatgcttc | ttttctctca | gtcttgtgtg | 1860 |
| tgcgcatata | cccactcata | gacatcttcg | tacgctgcac | tttccctccc | ttagcaagca | 1920 |
| gactcggccg | atatctttat | ggtcctcctc | ggttacgtcc | ttatgcacgg | cacattcgtc | 1980 |
| cgactgttcc | tcaactttcg | tcggatgggc | gcaaactttt | ggctgccagg | catggttctt | 2040 |
| gtctcgtcct | ccttttgcctt | cctcaccgcc | ctcctcgccg | cctcgatcct | caacgttccg | 2100 |
| atcgacccga | tctgtctctc | ggaagcactt | cccttcctcg | tgctcaccgt | cggatttgac | 2160 |
| aaggacttta | ccctcgcaaa | atctgtgttc | agctccccag | aaatcgcacc | cgtcatgctt | 2220 |

```
agacgaaagc cggtgatcca accaggagat gacgacgatc tcgaacagga cgagcacagc    2280
agagtggccg ccaacaaggt tgacattcag tgggcccctc cggtcgccgc ctcccgtatc    2340
gtcattggct cggtcgagaa gatcgggtcc tcgatcgtca gagactttgc cctcgaggtc    2400
gccgtcctcc ttctcggagc cgccagcggg ctcggcggac tcaaggagtt ttgtaagctc    2460
gccgcgttaa ttttggtggc cgactgctgc ttcacctttta ccttctatgt cgccatcctc   2520
accgtcatgg tcgaggtaag ccttttcttc aagtttcttg ctgtcatttt cctttcgaca    2580
cgtatgctca tctttcgttt ccgtctctct cacctttcca ggttcaccga atcaagatca    2640
tccggggctt ccgaccggcc cacaataacc gaacaccgaa tactgtgccc tctacccta    2700 ctatcgacgg tcaatctacc aacagatccg gcatctcgtc agggcctccg gcccgaccga    2760
ccgtgcccgt gtggaagaaa gtctggagga agctcatggg cccagagatc gattgggcgt    2820
ccgaagctga ggctcgaaac ccggttccaa agttgaagtt gctcttagta agtaaacttc    2880
ctttgttctt ctcatcattc tttatctccg aatcctgacg tcggacccct ctcgattcaa    2940
agatcttggc ctttcttatc cttcatatcc tcaacctttg cacgcctctg accgagacca    3000
cagctatcaa gcgatcgtct agcatacacc agcccattta tgccgaccct gctcatccga    3060
tcgcacagac aaaacgacg ctccatcggg cgcacagcct agtcatcttt gatcagttcc     3120
ttagtgactg gacgaccatc gtcggagatc caatcatgag caagtggatc atcatcaccc    3180
tgggcgtgtc catcctgctg aacggggtcc tcctaaaagg gatcgcttct ggctctgctc    3240
tcggacccgg tcgtgccgga ggaggaggag ctgccgccgc cgccgccgtc ttgctcggag    3300
cgtgggaaat cgtcgattgg aacaatgaga cagagacctc aacgaacact ccggctggtc    3360
cacccggcca caagaaccag aatgtcaacc tccgactcag tctcgagcgg gatactggtc    3420
tcctccgtta ccagcgtgag caggcctacc aggcccagtc tcagatcctc gctcctatt    3480 caccggtctc tgtcgcgccc gtcgtctcca acggtaacgg taacgcatcg aaatcgattg    3540
agaaaccaat gcctcgtttg gtggtcccta acggaccaag atccttgcct gaatcaccac    3600
cttcgacgac agaatcaacc ccggtcaaca aggttatcat cggtggaccg tccgacaggc    3660
ctgccctaga cggactcgcc aatggaaacg gtgccgtccc ccttgacaaa caaactgtgc    3720
ttggcatgag gtcgatcgaa gaatgcgaag aaattatgaa gagtggtctc gggccttact    3780
cactcaacga cgaagaattg attttgttga ctcaaaaggg aaagattccg ccgtactcgc    3840
tggaaaaagc attgcagaac tgtgagcggg cggtcaagat tcgaagggcg gttatctgta    3900
ggtctttttc tcctttgaat ttcaagcctt ggaggagagg aaagtgcttc ggggtacaat    3960
acaggttgtg caaacaaacc aagagaaact aaagaaaact ttcttctcct ctctctcccc    4020
tcgacgtcag cccgagcatc cgttactaag acgctggaaa cctcggactt gcccatgaag    4080
gattacgact actcgaaagt gatgggcgca tgctgtgaga acgttgtcgg atatatgcct    4140
ctccctgtcg gaatcgctgg tccacttaac attgatggcg aggtcgtccc catcccgatg    4200
gccaccaccg agggaactct cgtggcctcg acgtcgagag gttgcaaagc gctcaacgcg    4260
ggtggcggag tgaccaccgt catcacccag gatgcgatga cgagaggacc ggtggtggat    4320
ttcccttcgg tctctcaggc cgcacaggcc aaacgatggt tggattcggt cgaaggaatg    4380
gaggttatgg ccgcttcgtt caactcgact tctagattcg ccaggttgca gagcatcaag    4440
tgtggaatgg ccggccgatc gctatacatc cgtttggcga ccagtaccgg agatgcgatg    4500
ggaatgaaca tggctggtga gtgcgacgag ttttctttgt tcttcttgtg cggaccatgt    4560
```

-continued

```
tttctcatcc agccaattca ttcttcattc cttctcggtg tttggcaacc ttttaggtaa    4620
aggaacggag aaagctttgg aaaccctgtc cgagtacttc ccatccatgc agatccttgc    4680
tctttctggt aactactgta tcgacaagaa gccttctgcc atcaactgga ttgagggccg    4740
tggaaagtcc gtggtggccg agtcggtgat ccctggagcg atcgtcaagt ctgtcctcaa    4800
gacaacggtt gcggatctcg tcaacttgaa cattaagaaa aacttgatcg gaagtgccat    4860
ggcaggcagc attggaggat tcaacgccca cgcgtcgaat attttgactg tgcgtacttc    4920
tctttccata ttcgtcctcg tttaatttct tttctgtcca gtcttatgac gtctgattgg    4980
ttcttctttt cacccacaca catacagtca atcttcttgg ctacaggtca ggatcctgca    5040
cagaatgtgg agtcctcaat gtgcatgaca ttgatggagg cgtacgtttt ttgttttgtt    5100
ttccttcttt ttccatatgt ttctacttct actttcttcc cgagtccgcc aagctgatac    5160
ctttatacgg tccttctctt tctcatgacg agtagtgtga acgacggaaa agatctactc    5220
atcacctgct cgatgccggc gatcgagtgc ggaacggtcg gtggaggaac tttcctccct    5280
ccgcaaaacg cctgtttgca gatgctcggt gtcgcaggtg cccatccaga ttcgcccggt    5340
cacaatgctc gtcgactagc aagaatcatc gctgccagtg tgatggctgg agagttgagt    5400
ttgatgagtg ctttggccgc tggtcattta atcaaggccc acatgagtaa gtctgccacc    5460
ttttgataat caaaagggtc gtggtactgg tgtcactgac tggtgactct tcctgtcatg    5520
cagagcacaa tcgatcgaca ccttcgactc ctctaccggt ctcaccgttg cgacccgac    5580 cgaacacgcc gtcccaccgg tcgattggat tgctcacacc gatgacgtct tccgcatcgg    5640
tcgcctcgat gttctctggg ttcggtagtc cgtcgacgag ctcgctcaag acggtaggta    5700
gcatggcttg cgtcagggaa cgaggggacg agacgagtgt gaacgtggat gcctgaactg    5760
gggactccct tttcttggta tcccttccgt ttttctttcg cctttgaat cctgtattct    5820 tgtccgtttt ttcatcttct cttcctggtt ctccttctct cgttcatctg caaaaacaaa    5880
attcaatcgc atcggtctct ggcattccat ttgggtttca aaatcaaatc aatctctatc    5940
tactatctca aatatctttt tttcatcttt tgattcattt ctgttgaaaa ctgtcttgcc    6000
cttctcctac ttcttatctc tgccttcttg ccaaagttca attcgttgtc catctgtgca    6060
ctctgatcta tcagtctgta tcaagtacgc tcttaaatct gtaattggct ctcggaggtg    6120
tctcgtcatc tcacatatgg ctggcgatat gatgtgtcgg tttcttcccc tccaacaaag    6180
gcgacgtggc tccttcatca atctttggcg caagctctca aaattctcca aaacggctga    6240
ctaagcaagg tttccaagta ctctcaaacc gagcaaggcc atccatcctc aaatcaactt    6300
gtgaaaccct ttgtggatag accgtccaaa ccgagctctt cccaatcttc gcctccccttt    6360 cttcctgcag                                                            6370
```

<210> SEQ ID NO 3  
<211> LENGTH: 4135  
<212> TYPE: DNA  
<213> ORGANISM: Phaffia rhodozyma  
<220> FEATURE:  
<221> NAME/KEY: 5'UTR  
<222> LOCATION: (911)..(912)  
<223> OTHER INFORMATION: EXPERIMENTAL  
<221> NAME/KEY: exon  
<222> LOCATION: (1021)..(1124)  
<221> NAME/KEY: intron  
<222> LOCATION: (1125)..(1630)  
<221> NAME/KEY: exon  
<222> LOCATION: (1631)..(1956)  
<221> NAME/KEY: intron  
<222> LOCATION: (1957)..(2051)

<221> NAME/KEY: exon
<222> LOCATION: (2052)..(2366)
<221> NAME/KEY: intron
<222> LOCATION: (2367)..(2446)
<221> NAME/KEY: exon
<222> LOCATION: (2447)..(2651)
<221> NAME/KEY: intron
<222> LOCATION: (2652)..(2732)
<221> NAME/KEY: exon
<222> LOCATION: (2733)..(3188)
<221> NAME/KEY: polyA_site
<222> LOCATION: (3284)..(3285)

<400> SEQUENCE: 3

```
actgactcgg ctaccggaaa atatcttttc aggacgcctt gatcgttttg gacaacacca      60
tgatgtcacc atatcttcag cggccgttgg agctaggagt agacattgta tacgactctg     120
gaacaaagta tttgagtgga caccacgatc tcatggctgg tgtgattact actcgtactg     180
aggagattgg gaaggttcgt gcttgcttgc tttgaatgtc gtgcctaaag ccattgccat     240
aagacagagt ctgatctatg tcgtttgcct acaacagaga atggcctggt tcccaaatgc     300
tatgggaaat gcattgtctc cgttcgactc gttccttctt ctccgaggac tcaaaacact     360
tcctctccga ctggacaagc agcaggcctc atctcacctg atcgcctcgt acttacacac     420
cctcggcttt cttgttcact accccggtct gccttctgac cctgggtacg aacttcataa     480
ctctcaggcg agtggtgcag gtgccgtcat gagctttgag accggagata tcgcgttgag     540
tgaggccatc gtgggcggaa cccgagtttg gggaatcagt gtcagtttcg gagccgtgaa     600
cagtttgatc agcatgcctt gtctaatgag gttagttctt atgccttctt ttcgcgcctt     660
ctaaaatttc tggctgacta attgggtcgg tctttccgtt cttgcatttc agtcacgcat     720
ctattcctgc tcaccttcga gccgagcgag gtctccccga acatctgatt cgactgtgtg     780
tcggtattga ggaccctcac gatttgcttg atgatttgga ggcctctctt gtgaacgctg     840
gcgcaatccg atcagtctct acctcagatt catcccgacc gctcactcct cctgcctctg     900
attctgcctc ggacattcac tccaactggg ccgtcgaccg agccagacag ttcgagcgtg     960
ttaggccttc taactcgaca gccggcgtcg aaggacagct tgccgaactc aatgtagacg    1020
atgcagccag acttgcgggc gatgagagcc aaaaagaaga aattcttgtc agtgcaccgg    1080
gaaaggtcat tctgttcggc gaacatgctg taggccatgg tgttgtgagt gagaaatgaa    1140
agctttatgc tctcattgca tcttaacttt tcctcgcctt ttttgttctc ttcatcccgt    1200
cttgattgta gggatgcccc cctttgcccc tttccccttc ttgcatctgt ctatatttcc    1260
ttatacattt cgctcttaag agcgtctagt tgtaccttat aacaaccttt ggttttagca    1320
tcctttgatt attcatttct ctcatccttc ggtcagaggc tttcggccat ctttacgtct    1380
gattagattg taatagcaag aactatcttg ctaagccttt tctcttcctc ttcctcctat    1440
ataaatcgaa ttcactttcg gacatgttta ttttggggaa atcatcaagg ggtgggggc     1500
caatcccgac actaattttc tgctcacgtc aaaactcagc gttcagaatc agtcactgac    1560
cctgatacgt gtctctatgt gtgtgggtgt acgtgcgaat tgtgactcga cgttctacgc    1620
ttaaaaacag accgggatcg ctgcttccgt tgatcttcga tgctacgctc ttctctcacc    1680
cactgctacg acaacaacat catcgtcgtt atcgtctaca acattacca tctccctaac     1740
ggacctgaac tttacgcagt cttggcctgt tgattctctt ccttggtcac ttgcgcctga    1800
ctggactgag gcgtctattc cagaatctct ctgcccgaca ttgctcgccg aaatcgaaag    1860
gatcgctggt caaggtggaa acggaggaga aagggagaag gtggcaacca tggcattctt    1920
```

```
gtatttgttg gtgctattga gcaaagggaa gccaaggtag gttttttctg tctcttcttt    1980
ttgcctataa agactcttaa ctgacggaga aagtgttggg tttcttcctt cgggggttca    2040
atcaattaaa gtgagccgtt cgagttgacg gctcgatctg cgcttccgat gggagctggt    2100
ctgggttcat ccgccgctct atcgacctct cttgccctag tctttcttct ccactttttct   2160 cacctcagtc caacgacgac tgcagagaaa tcaacaatcc cgacggccga cacagaagta    2220
attgacaaat gggcgttctt agctgaaaaa gtcatccatg gaaatccgag tgggattgat    2280
aacgcggtca gtacgagagg aggcgctgtt gcttccaaaa gaaagattga gggaaaacag    2340
gaaggtggaa tggaagcgat caagaggtac gcagacacgg tgcttcatat gccatactcc    2400
agtctgattg acccatgatg aacgtctttc tacatttcga atatagcttc acatccattc    2460
gattcctcat cacagattct cgtatcggaa gggatacaag atctctcgtt gcaggagtga    2520
atgctcgact gattcaggag ccagaggtga tcgtcccttt gttggaagcg attcagcaga    2580
ttgccgatga ggctattcga tgcttgaaag attcagagat ggaacgtgct gtcatgatcg    2640
atcgacttca agttagttct tgttcctttc aagactcttt gtgacattgt gtcttatcca    2700
tttcatcttc ttttttcttc cttcttctgc agaacttggt ctccgagaac cacgcacacc    2760
tagcagcact tggcgtgtcc cacccatccc tcgaagagat tatccggatc ggtgctgata    2820
agcctttcga gcttcgaaca aagttgacag gcgccggtgg aggtggttgc gctgtaaccc    2880
tggtgcccga tggtaaagtc tctccttttc tcttccgtcc aagcgacaca tctgaccgat    2940
gcgcatcctg tacttttggt caaccagact tctcgactga aaccctcaa gctcttatgg     3000 agacgctcgt tcaatcatcg ttcgcccctt atattgcccg agtgggtggt tcaggcgtcg    3060
gattcctttc atcaactaag gccgatccgg aagatgggga gaacagactt aaagatgggc    3120
tggtgggaac ggagattgat gagctagaca gatgggcttt gaaaacgggt cgttggtctt    3180
ttgcttgaac gaaagatagg aaacggtgat tagggtacag atcctttgct gtcattttta    3240
caaaacactt tcttatgtct tcatgactca acgtatgccc tcatctctat ccatagacag    3300
cacggtacct ctcaggtttc aatacgtaag cgttcatcga caaacatgc ggcacacgaa     3360 aacgagtgga tataagggag aagagagata ttagagcgaa aaagagaaga gtgagagagg    3420
aaaaaaataa ccgagaacaa cttattccgg tttgttagaa tcgaagatcg agaaatatga    3480
agtacatagt ataaagtaaa gaagagaggt ttacctcaga ggtgtgtacg aaggtgagga    3540
caggtaagag gaataattga ctatcgaaaa aagagaactc aacagaagca ctgggataaa    3600
gcctagaatg taagtctcat cggtccgcga tgaaagagaa attgaaggaa gaaaaagccc    3660
ccagtaaaca atccaaccaa cctcttggac gattgcgaaa cacacacacg cacgcggaca    3720
tatttcgtac acaaggacgg gacattcttt ttttatatcc gggtggggag agagagggtt    3780
atagaggatg aatagcaagg ttgatgtttt gtaaaaggtt gcagaaaaag gaaagtgaga    3840
gtaggaacat gcattaaaaa cctgcccaaa gcgatttata tcgttcttct gttttcactt    3900 cttttccgggc gctttcttag accgcggtgg tgaaggggtta ctcctgccaa ctagaagaag   3960
caacatgagt caaggattag atcatcacgt gtctcatttg acgggttgaa agatatattt    4020
agatactaac tgcttcccac gccgactgaa aagatgaatt gaatcatgtc gagtggcaac    4080
gaacgaaaga acaaatagta agaatgaatt actagaaaag acagaatgac tagaa         4135
```

<210> SEQ ID NO 4
<211> LENGTH: 2767
<212> TYPE: DNA
<213> ORGANISM: Phaffia rhodozyma -continued

```
<220> FEATURE:
<221> NAME/KEY: 5'UTR
<222> LOCATION: (372)..(373)
<223> OTHER INFORMATION: EXPERIMENTAL
<221> NAME/KEY: exon
<222> LOCATION: (401)..(451)
<221> NAME/KEY: intron
<222> LOCATION: (452)..(633)
<221> NAME/KEY: exon
<222> LOCATION: (634)..(876)
<221> NAME/KEY: intron
<222> LOCATION: (877)..(1004)
<221> NAME/KEY: exon
<222> LOCATION: (1005)..(1916)
<221> NAME/KEY: polyA_site
<222> LOCATION: (2217)..(2218)

<400> SEQUENCE: 4
gaattcttcc cgactgggct gatcgacttg actggaagat ctaaggcgga gggatgaagg      60
aagtaattgg agggaatgag gaaaaaaaaa ggcgagggaa cgcggtcttc tttcctggca     120
aggcaatgtc gtgtatctct cttgattctt tcgttgtatc gacggaccac actcttttcg     180
aatgaatatc actatcgcat ccaatgatcg ctatacatgg catttacata tgccagacat     240
cgctgagaaa gagagaacat tcctttggaa aaagcctact gtgcctgaag tcaggctgat     300
gttgattaaa cgtctttccc catcctaagc agacaaacaa cttcttttcg ttcaacacac     360
cacctctctc cgaaaaagct cttcaatcca gtccattaag atggttcata tcgctactgc     420
ctcggctccc gttaacattg cgtgtatcaa gtccgtctg cattgtgaat gctgctcgtt      480
tgccttgtgt gcgtttggtg gatctgaaag aacccttgct tgaaccattc catctctgct     540
cttttcttc ctgtccttt cttttctca cgacaaaaaa accacctgga ccctttgtgt        600
tcctttccat tggtgttcat acacctaaca cagtactggg gtaaacggga taccaagttg     660
attctccta caaactcctc cttgtctgtc actctcgacc aggatcacct ccgatcgacg      720
acgtcttctg cttgtgacgc ctcgttcgag aaggatcgac tttggcttaa cgggatcgag     780
gaggaggtca aggctggtgg tcggttggat gtctgcatca aggagatgaa gaagcttcga     840
gcgcaagagg aagagaagga tgccggtctg gagaaagtga gttttctcc tgtgtgcgtg      900
tgtactctgt ataggtaccg ttgacaggac agtctttctg aagagtttgg atcttactct     960
tttttggggg ggtggtggtg tttgaaataa tgaccaaaat aaagctctca tctttcaacg    1020
tgcaccttgc gtcttacaac aacttcccga ctgccgctgg acttgcttcc tccgcttccg    1080
gtctagctgc gttggtcgcc tcgctcgcct cgctctacaa cctcccaacg aacgcatccg    1140
aactctcgct catcgcccga caaggttctg gttctgcctg ccgatcgctc ttcggcgggt    1200
tcgttgcttg ggaacagggc aagctttcct ctggaaccga ctcgttcgct gttcaggtcg    1260
agcccaggga acactggccc tcactccacg cgctgatctg tgtagtttcc gacgagaaaa    1320
agacgacggc ctcgacggca ggcatgcaaa ccacggtgaa cacctcgcct ttgctccaac    1380
accgaatcga acacgtcgtt ccagcccgga tggaggccat cacccaggcg atccgggcca    1440
aggatttcga ctcgttcgca aagatcacca tgaaggactc caaccagttc cacgccgtct    1500
gcctcgattc ggaaccccg atcttttact tgaacgatgt ctcccgatcg atcatccatc     1560
tcgtcaccga gctcaacaga gtgtccgtcc aggccggcgg tcccgtcctt gccgcctaca    1620
cgttcgacgc cgggccgaac gcggtgatct acgccgagga atcgtccatg ccggagatca    1680
tcaggttaat cgagcggtac ttcccgttgg gaacggcttt cgagaacccg ttcggggtta    1740
acaccgaagg cggtgatgcc ctgagggaag gctttaacca gaacgtcgcc ccggtgttca    1800
```

-continued

```
ggaagggaag cgtcgcccgg ttgattcaca cccggatcgg tgatggaccc aggacgtatg    1860
gcgaggagga gagcctgatc ggcgaagacg gtctgccaaa ggtcgtcaag gcttagacta    1920
taggttgttt cttctaaatt tgagccttcc tcccgcctcc cttccacaag cataaaacaa    1980
aggataaaca aatgaattat caaataact ataggttgtt tcttctaaat ttgagccttc     2040
ctcccgcctc ccttccacaa gcataaaaca aaggataaac aaatgaatta tcaaaataaa    2100
ataaaaagtc tgccttcttt gttttggaat acatcttctt tgggacatga cccttctcct    2160
tcttttccgt atacatcttt ttgggtattt catggtgatc aaacaacatt gtgatcgaaa    2220
gcagagacgg ccatggtgct ggctttgagc gtctggcgtt ttgtgtgtcc tgcacttgag    2280
caaccccaag ctgaccgcta ggaaaactca ttgatgtgat ttatatcgta cgatgaaaga    2340
gaataaaatg atagaagaac aaagaagaac aaagtagaag aacgtctgag aagaaagaca    2400
ggaaaatgac acgtacatag tgttcgatga tgaatgatat aatattaaat ataaaatgag    2460
gtaaacgtat agcatcacgg gatgaacgga tgaacatgta gtggacaagg ttgggaaata    2520
ggaatgtaga atccaagaat cgttgactga tggacgacg tatgtaaaca ggtacacccc     2580
aaagaaaaga aagaaagaaa gaaagaaaac acaaagccaa ggaagtaaag cagatggtct    2640
tctaagaata cggcttcaaa aagacagtga acactcgtcg tcgaggaatg acaagaaaag    2700
tgagagacta cgaaaggaag aaaccaagac gaaaagaaga acggagatcg aacggacaga    2760
aataaag                                                             2767
```

```
<210> SEQ ID NO 5
<211> LENGTH: 4092
<212> TYPE: DNA
<213> ORGANISM: Phaffia rhodozyma
<220> FEATURE:
<221> NAME/KEY: 5'UTR
<222> LOCATION: (787)..(788)
<223> OTHER INFORMATION: EXPERIMENTAL
<221> NAME/KEY: exon
<222> LOCATION: (852)..(986)
<221> NAME/KEY: intron
<222> LOCATION: (987)..(1173)
<221> NAME/KEY: exon
<222> LOCATION: (1174)..(1317)
<221> NAME/KEY: intron
<222> LOCATION: (1318)..(1468)
<221> NAME/KEY: exon
<222> LOCATION: (1469)..(1549)
<221> NAME/KEY: intron
<222> LOCATION: (1550)..(1671)
<221> NAME/KEY: exon
<222> LOCATION: (1672)..(1794)
<221> NAME/KEY: intron
<222> LOCATION: (1795)..(1890)
<221> NAME/KEY: exon
<222> LOCATION: (1891)..(1979)
<221> NAME/KEY: intron
<222> LOCATION: (1980)..(2092)
<221> NAME/KEY: exon
<222> LOCATION: (2093)..(2165)
<221> NAME/KEY: intron
<222> LOCATION: (2166)..(2250)
<221> NAME/KEY: exon
<222> LOCATION: (2251)..(2391)
<221> NAME/KEY: intron
<222> LOCATION: (2392)..(2488)
<221> NAME/KEY: exon
<222> LOCATION: (2489)..(2652)
<221> NAME/KEY: intron
<222> LOCATION: (2653)..(2784)
<221> NAME/KEY: exon
<222> LOCATION: (2785)..(2902)
<221> NAME/KEY: polyA_site
<222> LOCATION: (3024)..(3025)
```

<400> SEQUENCE: 5

```
cgcccggtat cttgccacag atgccgccgg agtgtctggc ggagtgctag gaacaacgtc      60
atctccatct gacgagcaag cgtaccacaa gctagctctt cgtctgtcag aaggacatcc     120
acgcaccttc ctggccttcg gggatggcac cttctcgtcg acttcccatg gccgtgcccc     180
tggccttgtg aagatactgt ttgccaagct gagcgcctcc ccgctgctcc aggtccgcaa     240
ggtccgagag tattggacgt cgaagatatg ttcaaagtgt caggcgagtt ctcgggagaa     300
aaaaaaagcg tgggctctga aacagtgtgg aaatgtctac aaagtgagct ggatttattg     360
tgtgtgtatg tgtgtgtgtg tgtatgttct gtgttggttg ctcactgtac tctatgctct     420
ctcttagatt tggggaacag tgctgtgaac gcgtcgcgaa acatgctgca cctagcctt      480
caccagaagg agaaccagag ggcgggaatg ctggtgtctg acgctgctac tgctgctacg     540
ctagccgctg aggctgaggc tggcagaaac taaatccatg acccatcaga tcttggtgat     600
tcgtggtctg aggacaccca agtccaaaag ggctatatat cgaccatcat ccgttgcggt     660
cactcagtag taactaaagc tatacatagg aatgttctga acttgataac cctaacacta     720
cgaaaatatc tcggaaaata gattaatttc cttctcatct caaacaaaag acacaacacc     780
atcaatcacg ctccttttcac acactctcct ttttgctctc tcgttcgaca gaaaataaca     840
tcaatagcca aatgtccact acgcctgaag agaagaaagc agctcgagca agttcgagg     900
ctgtcttccc ggtcattgcc gatgagattc tcgattatat gaagggtgaa ggcatgcctg     960
ccgaggcttt ggaatggatg aacaaggttc gtcaagggtt tcttctttat tcttctggtc    1020
tttgtttcgg tcgaactggc tttcgaactt ggccttgacc ggttggatct cggttgttgc    1080
gccaaaacga tgtcgaagca aaacttactc ttacctgttc ggtttccttc cttccgacct    1140
tctctctacc cttgcctccg atcggtctta tagaacttgt actacaacac tcccggagga    1200
aaactcaacc gaggactttc cgtggtggat acttatatcc ttctctcgcc ttctggaaaa    1260
gacatctcgg aagaagagta cttgaaggcc gctatcctcg gttggtgtat cgagcttgta    1320
cgcgttttct tcattcacct ttcttctcg tcttctactc tcttctctcg aactatcttc    1380
cctgcgtgtc atcctacacg aatctttata cttacatgtt ggaacatatg ccctgttctt    1440
aattcacctc ttttgtctcg gatggtagct ccaagcttac ttcttggtgg ctgatgatat    1500
gatggacgcc tcaatcaccc gacgaggcca accctgttgg tacaaagttg ttagtcccctt   1560
cttctctttc tgtcctcttt cttctgagct atgccaattc ttgattgaaa tcggtggtgc    1620
cgtccggact aatccgtttg tcgttttat catatcttct tgcacaaaca ggagggagtg    1680
tctaacattg ccatcaacga cgcgttcatg ctcgagggag ctatctactt tttgctcaag    1740
aagcacttcc gaaagcagag ctactatgtc gatctgctag agctcttcca cgatgtttgt    1800
ctctatttct tttcttcctc ccctcaataa actgtatttg tgaccattct ggatcctttc    1860
ctgacgatga atcattcttc ggatgagtag gttactttcc aaaccgagtt gggacagctc    1920
atcgatctgt tgaccgctcc tgaggatcac gtcgatctcg acaagttctc ccttaacaag    1980
tatgcccgtc atatattcgt tttgttgcat tcacgtctga ttgtcagctc cgattattga    2040
ctctgatggt gatggtattg accacatcat gcgatgtttg actttctcgt aggcaccacc    2100
tcatcgttgt ttacaagacc gctttctatt cattctacct tcctgtcgca ctcgctatgc    2160
gaatggtggg tctctctctt caactgttct tcctgatttt cttgaccatc tgtaacataa    2220
atccttggaa ttttgaactc tatgtcatag gtcggcgtga cagatgagga ggcgtacaag    2280
```

-continued

```
cttgcgctct cgatcctcat cccgatgggt gaatactttc aagttcagga tgatgtgctc    2340
gacgcgttcg ctcctccgga gatccttgga aagatcggaa ccgacatctt ggtgcgtttt    2400
cgttccttcc ttctacgttc tgttttctat cttctgactc cccgtccatc atttatgctt    2460
ctgttaaaac gtattgaaac atcaaaagga caacaaatgt tcatggccta tcaaccttgc    2520
actctctctc gcctcgcccg ctcagcgaga gattctcgat acttcgtacg gtcagaagaa    2580
ctcggaggca gaggccagag tcaaggctct gtacgctgag cttgatatcc agggaaagtt    2640
caacgcttat gagtatgtca tctttttttaa attttctaat tttcttttca tctcttgttc    2700
ccaagaatta ttttgtgaaa gttctgggac tgaacatggt gcatcccttt gggttcactc    2760
cgcatatgtc tcccgtttga ataggcaaca gagttacgag tcgctgaaca agttgattga    2820
cagtattgac gaagagaaga gtggactcaa gaaagaagtc ttccacagct tcctgggtaa    2880
ggtctataag cgaagcaagt aattctcctc tttatatgca aagggaagat tttggcggga    2940
gtgataggta ggaagagaag ggagggtcat attcattagg catttctctt gcagatatag    3000
atgatcaaaa agggatatcg gtcctcttct tgttccgaa tacataataa gtcatacgaa    3060
gccgaacatg acaaaagtgg ttcatgagat caaacttttt gcatgatctt ctgcgatttt    3120
gtacaattct ctcgcatcct attaggatcg aaccaggaga agatgagaga aggaaaccct    3180 cacccccgtca gataacaaac gagaagtctc atcacacaca cacacagatg aaagagaaaa    3240
ataaactgac gaggataact tccaatccga tttttccagc ccacgaacct tccttggtcc    3300
ccgctccggt gccttcgagt ccgatcaatg gggcccaaac gcctgaagat ccaaagaacc    3360
cttgttgagg tgtatttctc gtctgagcaa tcttagatcc ttcaatttgc agtcgcgcat    3420
atataccatc aacatcatcg tcatcaccat cattgtcgtc cacaacagca ccgcaacgcc    3480
gttaatggca gggcttggac aacttgaggc ggtttctagc aggtcggacc gattggagct    3540
cgacccaggg tgcacatcac caagacacat tctccttcaa atgagcgaac aagacataat    3600
gagggaagta gtacgctatc gaacgtcttc tcacatcccg ggttcttggc gtatcttttg    3660
gcgattcttt ttgttgaaat agaaaattga agagaaaaaa agagatccac atgatgaaga    3720
acggctctgt agattcatgc tcgaaagaaa gaaagaaaga aaagaggggg aacgaacgga    3780
tctgaatctg tggccaacca aaagtaggca caaagatga caacagcgcc ctcttcgaca    3840
agtctttgaa ctgcttgtgg atgagacaag tcccagcaga tcaacattcc tgctttaccc    3900
catggagtat caaacacctg agaataggtc ttgcccggct gtagataatc tctgaccgt    3960 catatgcgcg aaacgatcag tacgaccgac tctactcgaa gtcgtcaaga gcacggacga    4020
gaacgaaaag aggacaaacc gctctggatg ccataaattt ctcttctcat acctctccca    4080
cccaccctca gg                                                       4092
```

```
<210> SEQ ID NO 6
<211> LENGTH: 467
<212> TYPE: PRT
<213> ORGANISM: Phaffia rhodozyma

<400> SEQUENCE: 6
```

Met Tyr Thr Ser Thr Thr Glu Gln Arg Pro Lys Asp Val Gly Ile Leu
1               5                   10                  15

Gly Met Glu Ile Tyr Phe Pro Arg Arg Ala Ile Ala His Lys Asp Leu
            20                  25                  30

Glu Ala Phe Asp Gly Val Pro Ser Gly Lys Tyr Thr Ile Gly Leu Gly
        35                  40                  45

```
Asn Asn Phe Met Ala Phe Thr Asp Asp Thr Glu Asp Ile Asn Ser Phe
     50                  55                  60

Ala Leu Asn Ala Val Ser Gly Leu Leu Ser Lys Tyr Asn Val Asp Pro
 65                  70                  75                  80

Lys Ser Ile Gly Arg Ile Asp Val Gly Thr Glu Ser Ile Ile Asp Lys
                 85                  90                  95

Ser Lys Ser Val Lys Thr Val Leu Met Asp Leu Phe Glu Ser His Gly
            100                 105                 110

Asn Thr Asp Ile Glu Gly Ile Asp Ser Lys Asn Ala Cys Tyr Gly Ser
            115                 120                 125

Thr Ala Ala Leu Phe Asn Ala Val Asn Trp Ile Glu Ser Ser Ser Trp
130                 135                 140

Asp Gly Arg Asn Ala Ile Val Phe Cys Gly Asp Ile Ala Ile Tyr Ala
145                 150                 155                 160

Glu Gly Ala Ala Arg Pro Ala Gly Gly Ala Gly Ala Cys Ala Ile Leu
                165                 170                 175

Ile Gly Pro Asp Ala Pro Val Val Phe Glu Pro Val His Gly Asn Phe
            180                 185                 190

Met Thr Asn Ala Trp Asp Phe Tyr Lys Pro Asn Leu Ser Ser Glu Tyr
            195                 200                 205

Pro Ile Val Asp Gly Pro Leu Ser Val Thr Ser Tyr Val Asn Ala Ile
    210                 215                 220

Asp Lys Ala Tyr Glu Ala Tyr Arg Thr Lys Tyr Ala Lys Arg Phe Gly
225                 230                 235                 240

Gly Pro Lys Thr Asn Gly Val Thr Asn Gly His Thr Glu Val Ala Gly
                245                 250                 255

Val Ser Ala Ala Ser Phe Asp Tyr Leu Leu Phe His Ser Pro Tyr Gly
            260                 265                 270

Lys Gln Val Val Lys Gly His Gly Arg Leu Leu Tyr Asn Asp Phe Arg
            275                 280                 285

Asn Asn Pro Asn Asp Pro Val Phe Ala Glu Val Pro Ala Glu Leu Ala
    290                 295                 300

Thr Leu Asp Met Lys Lys Ser Leu Ser Asp Lys Asn Val Glu Lys Ser
305                 310                 315                 320

Leu Ile Ala Ala Ser Lys Ser Ser Phe Asn Lys Gln Val Glu Pro Gly
                325                 330                 335

Met Thr Thr Val Arg Gln Leu Gly Asn Leu Tyr Thr Ala Ser Leu Phe
            340                 345                 350

Gly Ala Leu Ala Ser Leu Phe Ser Asn Val Pro Gly Asp Glu Leu Val
            355                 360                 365

Gly Lys Arg Ile Ala Leu Tyr Ala Tyr Gly Ser Gly Ala Ala Ala Ser
    370                 375                 380

Phe Tyr Ala Leu Lys Val Lys Ser Ser Thr Ala Phe Ile Ser Glu Lys
385                 390                 395                 400

Leu Asp Leu Asn Asn Arg Leu Ser Asn Met Lys Ile Val Pro Cys Asp
                405                 410                 415

Asp Phe Val Lys Ala Leu Lys Val Arg Glu Glu Thr His Asn Ala Val
            420                 425                 430

Ser Tyr Ser Pro Ile Gly Ser Leu Asp Asp Leu Trp Pro Gly Ser Tyr
            435                 440                 445

Tyr Leu Gly Glu Ile Asp Ser Met Trp Arg Arg Gln Tyr Lys Gln Val
    450                 455                 460

Pro Ser Ala
```

465

<210> SEQ ID NO 7
<211> LENGTH: 1091
<212> TYPE: PRT
<213> ORGANISM: Phaffia rhodozyma

<400> SEQUENCE: 7

| Met | Tyr | Thr | Ile | Lys | His | Ser | Asn | Phe | Leu | Ser | Gln | Thr | Ile | Ser | Thr |
|---|---|---|---|---|---|---|---|---|---|---|---|---|---|---|---|
| 1 | | | | 5 | | | | | 10 | | | | | 15 | |

Gln Ser Thr Thr Ser Trp Val Val Asp Ala Phe Phe Ser Leu Gly Ser
            20                  25                  30

Arg Tyr Leu Asp Leu Ala Lys Gln Ala Asp Ser Ala Asp Ile Phe Met
        35                  40                  45

Val Leu Leu Gly Tyr Val Leu Met His Gly Thr Phe Val Arg Leu Phe
    50                  55                  60

Leu Asn Phe Arg Arg Met Gly Ala Asn Phe Trp Leu Pro Gly Met Val
65                  70                  75                  80

Leu Val Ser Ser Ser Phe Ala Phe Leu Thr Ala Leu Leu Ala Ala Ser
                85                  90                  95

Ile Leu Asn Val Pro Ile Asp Pro Ile Cys Leu Ser Glu Ala Leu Pro
            100                 105                 110

Phe Leu Val Leu Thr Val Gly Phe Asp Lys Asp Phe Thr Leu Ala Lys
        115                 120                 125

Ser Val Phe Ser Ser Pro Glu Ile Ala Pro Val Met Leu Arg Arg Lys
    130                 135                 140

Pro Val Ile Gln Pro Gly Asp Asp Asp Leu Glu Gln Asp Glu His
145                 150                 155                 160

Ser Arg Val Ala Ala Asn Lys Val Asp Ile Gln Trp Ala Pro Pro Val
                165                 170                 175

Ala Ala Ser Arg Ile Val Ile Gly Ser Val Glu Lys Ile Gly Ser Ser
            180                 185                 190

Ile Val Arg Asp Phe Ala Leu Glu Val Ala Val Leu Leu Leu Gly Ala
        195                 200                 205

Ala Ser Gly Leu Gly Gly Leu Lys Glu Phe Cys Lys Leu Ala Ala Leu
    210                 215                 220

Ile Leu Val Ala Asp Cys Cys Phe Thr Phe Thr Phe Tyr Val Ala Ile
225                 230                 235                 240

Leu Thr Val Met Val Glu Val His Arg Ile Lys Ile Arg Gly Phe
                245                 250                 255

Arg Pro Ala His Asn Asn Arg Thr Pro Asn Thr Val Pro Ser Thr Pro
            260                 265                 270

Thr Ile Asp Gly Gln Ser Thr Asn Arg Ser Gly Ile Ser Ser Gly Pro
        275                 280                 285

Pro Ala Arg Pro Thr Val Pro Val Trp Lys Val Trp Arg Lys Leu
    290                 295                 300

Met Gly Pro Glu Ile Asp Trp Ala Ser Glu Ala Glu Ala Arg Asn Pro
305                 310                 315                 320

Val Pro Lys Leu Lys Leu Leu Ile Leu Ala Phe Leu Ile Leu His
                325                 330                 335

Ile Leu Asn Leu Cys Thr Pro Leu Thr Glu Thr Thr Ala Ile Lys Arg
            340                 345                 350

Ser Ser Ser Ile His Gln Pro Ile Tyr Ala Asp Pro Ala His Pro Ile
        355                 360                 365

```
Ala Gln Thr Asn Thr Thr Leu His Arg Ala His Ser Leu Val Ile Phe
        370                 375                 380

Asp Gln Phe Leu Ser Asp Trp Thr Thr Ile Val Gly Asp Pro Ile Met
385                 390                 395                 400

Ser Lys Trp Ile Ile Ile Thr Leu Gly Val Ser Ile Leu Leu Asn Gly
                    405                 410                 415

Phe Leu Leu Lys Gly Ile Ala Ser Gly Ser Ala Leu Gly Pro Gly Arg
                420                 425                 430

Ala Gly Gly Gly Ala Ala Ala Ala Ala Val Leu Leu Gly Ala
            435                 440                 445

Trp Glu Ile Val Asp Trp Asn Asn Glu Thr Glu Thr Ser Thr Asn Thr
    450                 455                 460

Pro Ala Gly Pro Pro Gly His Lys Asn Gln Asn Val Asn Leu Arg Leu
465                 470                 475                 480

Ser Leu Glu Arg Asp Thr Gly Leu Leu Arg Tyr Gln Arg Glu Gln Ala
                485                 490                 495

Tyr Gln Ala Gln Ser Gln Ile Leu Ala Pro Ile Ser Pro Val Ser Val
                500                 505                 510

Ala Pro Val Val Ser Asn Gly Asn Gly Asn Ala Ser Lys Ser Ile Glu
                515                 520                 525

Lys Pro Met Pro Arg Leu Val Val Pro Asn Gly Pro Arg Ser Leu Pro
        530                 535                 540

Glu Ser Pro Pro Ser Thr Thr Glu Ser Thr Pro Val Asn Lys Val Ile
545                 550                 555                 560

Ile Gly Gly Pro Ser Asp Arg Pro Ala Leu Asp Gly Leu Ala Asn Gly
                565                 570                 575

Asn Gly Ala Val Pro Leu Asp Lys Gln Thr Val Leu Gly Met Arg Ser
                580                 585                 590

Ile Glu Glu Cys Glu Glu Ile Met Lys Ser Gly Leu Gly Pro Tyr Ser
                595                 600                 605

Leu Asn Asp Glu Glu Leu Ile Leu Leu Thr Gln Lys Gly Lys Ile Pro
            610                 615                 620

Pro Tyr Ser Leu Glu Lys Ala Leu Gln Asn Cys Glu Arg Ala Val Lys
625                 630                 635                 640

Ile Arg Arg Ala Val Ile Ser Arg Ala Ser Val Thr Lys Thr Leu Glu
                645                 650                 655

Thr Ser Asp Leu Pro Met Lys Asp Tyr Asp Tyr Ser Lys Val Met Gly
                660                 665                 670

Ala Cys Cys Glu Asn Val Val Gly Tyr Met Pro Leu Pro Val Gly Ile
                675                 680                 685

Ala Gly Pro Leu Asn Ile Asp Gly Glu Val Val Pro Ile Pro Met Ala
        690                 695                 700

Thr Thr Glu Gly Thr Leu Val Ala Ser Thr Ser Arg Gly Cys Lys Ala
705                 710                 715                 720

Leu Asn Ala Gly Gly Val Thr Thr Val Ile Thr Gln Asp Ala Met
                725                 730                 735

Thr Arg Gly Pro Val Val Asp Phe Pro Ser Val Ser Gln Ala Ala Gln
                740                 745                 750

Ala Lys Arg Trp Leu Asp Ser Val Glu Gly Met Glu Val Met Ala Ala
            755                 760                 765

Ser Phe Asn Ser Thr Ser Arg Phe Ala Arg Leu Gln Ser Ile Lys Cys
770                 775                 780

Gly Met Ala Gly Arg Ser Leu Tyr Ile Arg Leu Ala Thr Ser Thr Gly
```

-continued

```
                785                 790                 795                 800

Asp Ala Met Gly Met Asn Met Ala Gly Lys Gly Thr Glu Lys Ala Leu
                    805                 810                 815

Glu Thr Leu Ser Glu Tyr Phe Pro Ser Met Gln Ile Leu Ala Leu Ser
                820                 825                 830

Gly Asn Tyr Cys Ile Asp Lys Lys Pro Ser Ala Ile Asn Trp Ile Glu
            835                 840                 845

Gly Arg Gly Lys Ser Val Val Ala Glu Ser Val Ile Pro Gly Ala Ile
        850                 855                 860

Val Lys Ser Val Leu Lys Thr Thr Val Ala Asp Leu Val Asn Leu Asn
    865                 870                 875                 880

Ile Lys Lys Asn Leu Ile Gly Ser Ala Met Ala Gly Ser Ile Gly Gly
                    885                 890                 895

Phe Asn Ala His Ala Ser Asp Ile Leu Thr Ser Ile Phe Leu Ala Thr
                900                 905                 910

Gly Gln Asp Pro Ala Gln Asn Val Glu Ser Ser Met Cys Met Thr Leu
            915                 920                 925

Met Glu Ala Val Asn Asp Gly Lys Asp Leu Leu Ile Thr Cys Ser Met
        930                 935                 940

Pro Ala Ile Glu Cys Gly Thr Val Gly Gly Thr Phe Leu Pro Pro
    945                 950                 955                 960

Gln Asn Ala Cys Leu Gln Met Leu Gly Val Ala Gly Ala His Pro Asp
                    965                 970                 975

Ser Pro Gly His Asn Ala Arg Arg Leu Ala Arg Ile Ile Ala Ala Ser
                980                 985                 990

Val Met Ala Gly Glu Leu Ser Leu Met Ser Ala Leu Ala Ala Gly His
            995                1000                1005

Leu Ile Lys Ala His Met Lys His Asn Arg Ser Thr Pro Ser Thr Pro
        1010                1015                1020

Leu Pro Val Ser Pro Leu Ala Thr Arg Pro Asn Thr Pro Ser His Arg
    1025                1030                1035                1040

Ser Ile Gly Leu Leu Thr Pro Met Thr Ser Ser Ala Ser Val Ala Ser
                    1045                1050                1055

Met Phe Ser Gly Phe Gly Ser Pro Ser Thr Ser Ser Leu Lys Thr Val
                1060                1065                1070

Gly Ser Met Ala Cys Val Arg Glu Arg Gly Asp Glu Thr Ser Val Asn
            1075                1080                1085

Val Asp Ala
        1090

<210> SEQ ID NO 8
<211> LENGTH: 432
<212> TYPE: PRT
<213> ORGANISM: Phaffia rhodozyma

<400> SEQUENCE: 8

Lys Glu Glu Ile Leu Val Ser Ala Pro Gly Lys Val Ile Leu Phe Gly
    1               5                  10                  15

Glu His Ala Val Gly His Gly Val Thr Gly Ile Ala Ala Ser Val Asp
                20                  25                  30

Leu Arg Cys Tyr Ala Leu Leu Ser Pro Thr Ala Thr Thr Thr Thr Ser
            35                  40                  45

Ser Ser Leu Ser Ser Thr Asn Ile Thr Ile Ser Leu Thr Asp Leu Asn
        50                  55                  60
```

```
Phe Thr Gln Ser Trp Pro Val Asp Ser Leu Pro Trp Ser Leu Ala Pro
 65                  70                  75                  80

Asp Trp Thr Glu Ala Ser Ile Pro Glu Ser Leu Cys Pro Thr Leu Leu
                 85                  90                  95

Ala Glu Ile Glu Arg Ile Ala Gly Gln Gly Gly Asn Gly Gly Glu Arg
                100                 105                 110

Glu Lys Val Ala Thr Met Ala Phe Leu Tyr Leu Leu Val Leu Leu Ser
                115                 120                 125

Lys Gly Lys Pro Ser Glu Pro Phe Glu Leu Thr Ala Arg Ser Ala Leu
130                 135                 140

Pro Met Gly Ala Gly Leu Gly Ser Ser Ala Ala Leu Ser Thr Ser Leu
145                 150                 155                 160

Ala Leu Val Phe Leu Leu His Phe Ser His Leu Ser Pro Thr Thr Thr
                165                 170                 175

Gly Arg Glu Ser Thr Ile Pro Thr Ala Asp Thr Glu Val Ile Asp Lys
                180                 185                 190

Trp Ala Phe Leu Ala Glu Lys Val Ile His Gly Asn Pro Ser Gly Ile
                195                 200                 205

Asp Asn Ala Val Ser Thr Arg Gly Gly Ala Val Ala Phe Lys Arg Lys
210                 215                 220

Ile Glu Gly Lys Gln Glu Gly Gly Met Glu Ala Ile Lys Ser Phe Thr
225                 230                 235                 240

Ser Ile Arg Phe Leu Ile Thr Asp Ser Arg Ile Gly Arg Asp Thr Arg
                245                 250                 255

Ser Leu Val Ala Gly Val Asn Ala Arg Leu Ile Gln Glu Pro Glu Val
                260                 265                 270

Ile Val Pro Leu Leu Glu Ala Ile Gln Gln Ile Ala Asp Glu Ala Ile
                275                 280                 285

Arg Cys Leu Lys Asp Ser Glu Met Glu Arg Ala Val Met Ile Asp Arg
                290                 295                 300

Leu Gln Asn Leu Val Ser Glu Asn His Ala His Leu Ala Ala Leu Gly
305                 310                 315                 320

Val Ser His Pro Ser Leu Glu Glu Ile Ile Arg Ile Gly Ala Asp Lys
                325                 330                 335

Pro Phe Glu Leu Arg Thr Lys Leu Thr Gly Ala Gly Gly Gly Gly Cys
                340                 345                 350

Ala Val Thr Leu Val Pro Asp Asp Phe Ser Thr Glu Thr Leu Gln Ala
                355                 360                 365

Leu Met Glu Thr Leu Val Gln Ser Ser Phe Ala Pro Tyr Ile Ala Arg
370                 375                 380

Val Gly Gly Ser Gly Val Gly Phe Leu Ser Ser Thr Lys Ala Asp Pro
385                 390                 395                 400

Glu Asp Gly Glu Asn Arg Leu Lys Asp Gly Leu Val Gly Thr Glu Ile
                405                 410                 415

Asp Glu Leu Asp Arg Trp Ala Leu Lys Thr Gly Arg Trp Ser Phe Ala
                420                 425                 430
```

<210> SEQ ID NO 9
<211> LENGTH: 401
<212> TYPE: PRT
<213> ORGANISM: Phaffia rhodozyma

<400> SEQUENCE: 9

```
Met Val His Ile Ala Thr Ala Ser Ala Pro Val Asn Ile Ala Cys Ile
 1               5                  10                  15
```

-continued

```
Lys Tyr Trp Gly Lys Arg Asp Thr Lys Leu Ile Leu Pro Thr Asn Ser
             20                  25                  30

Ser Leu Ser Val Thr Leu Asp Gln Asp His Leu Arg Ser Thr Thr Ser
         35                  40                  45

Ser Ala Cys Asp Ala Ser Phe Glu Lys Asp Arg Leu Trp Leu Asn Gly
     50                  55                  60

Ile Glu Glu Val Lys Ala Gly Gly Arg Leu Asp Val Cys Ile Lys
 65                  70                  75                  80

Glu Met Lys Lys Leu Arg Ala Gln Glu Glu Lys Asp Ala Gly Leu
                 85                  90                  95

Glu Lys Leu Ser Ser Phe Asn Val His Leu Ala Ser Tyr Asn Asn Phe
             100                 105                 110

Pro Thr Ala Ala Gly Leu Ala Ser Ala Ser Gly Leu Ala Ala Leu
             115                 120                 125

Val Ala Ser Leu Ala Ser Leu Tyr Asn Leu Pro Thr Asn Ala Ser Glu
         130                 135                 140

Leu Ser Leu Ile Ala Arg Gln Gly Ser Gly Ser Ala Cys Arg Ser Leu
145                 150                 155                 160

Phe Gly Gly Phe Val Ala Trp Glu Gln Gly Lys Leu Ser Ser Gly Thr
                 165                 170                 175

Asp Ser Phe Ala Val Gln Val Glu Pro Arg Glu His Trp Pro Ser Leu
             180                 185                 190

His Ala Leu Ile Cys Val Val Ser Asp Glu Lys Lys Thr Thr Ala Ser
         195                 200                 205

Thr Ala Gly Met Gln Thr Thr Val Asn Thr Ser Pro Leu Leu Gln His
210                 215                 220

Arg Ile Glu His Val Val Pro Ala Arg Met Glu Ala Ile Thr Gln Ala
225                 230                 235                 240

Ile Arg Ala Lys Asp Phe Asp Ser Phe Ala Lys Ile Thr Met Lys Asp
                 245                 250                 255

Ser Asn Gln Phe His Ala Val Cys Leu Asp Ser Glu Pro Pro Ile Phe
             260                 265                 270

Tyr Leu Asn Asp Val Ser Arg Ser Ile Ile His Leu Val Thr Glu Leu
         275                 280                 285

Asn Arg Val Ser Val Gln Ala Gly Gly Pro Val Leu Ala Ala Tyr Thr
     290                 295                 300

Phe Asp Ala Gly Pro Asn Ala Val Ile Tyr Ala Glu Glu Ser Ser Met
305                 310                 315                 320

Pro Glu Ile Ile Arg Leu Ile Glu Arg Tyr Phe Pro Leu Gly Thr Ala
                 325                 330                 335

Phe Glu Asn Pro Phe Gly Val Asn Thr Glu Gly Gly Asp Ala Leu Arg
             340                 345                 350

Glu Gly Phe Asn Gln Asn Val Ala Pro Val Phe Arg Lys Gly Ser Val
         355                 360                 365

Ala Arg Leu Ile His Thr Arg Ile Gly Asp Gly Pro Arg Thr Tyr Gly
     370                 375                 380

Glu Glu Glu Ser Leu Ile Gly Glu Asp Gly Leu Pro Lys Val Val Lys
385                 390                 395                 400

Ala

<210> SEQ ID NO 10
<211> LENGTH: 355
<212> TYPE: PRT
```

```
<213> ORGANISM: Phaffia rhodozyma

<400> SEQUENCE: 10

Met Ser Thr Thr Pro Glu Glu Lys Lys Ala Ala Arg Ala Lys Phe Glu
 1               5                  10                  15

Ala Val Phe Pro Val Ile Ala Asp Glu Ile Leu Asp Tyr Met Lys Gly
                20                  25                  30

Glu Gly Met Pro Ala Glu Ala Leu Glu Trp Met Asn Lys Asn Leu Tyr
            35                  40                  45

Tyr Asn Thr Pro Gly Gly Lys Leu Asn Arg Gly Leu Ser Val Val Asp
        50                  55                  60

Thr Tyr Ile Leu Leu Ser Pro Ser Gly Lys Asp Ile Ser Glu Glu Glu
65                  70                  75                  80

Tyr Leu Lys Ala Ala Ile Leu Gly Trp Cys Ile Glu Leu Leu Gln Ala
                85                  90                  95

Tyr Phe Leu Val Ala Asp Asp Met Met Asp Ala Ser Ile Thr Arg Arg
                100                 105                 110

Gly Gln Pro Cys Trp Tyr Lys Val Glu Gly Val Ser Asn Ile Ala Ile
            115                 120                 125

Asn Asn Ala Phe Met Leu Glu Gly Ala Ile Tyr Phe Leu Leu Lys Lys
130                 135                 140

His Phe Arg Lys Gln Ser Tyr Tyr Val Asp Leu Leu Glu Leu Phe His
145                 150                 155                 160

Asp Val Thr Phe Gln Thr Glu Leu Gly Gln Leu Ile Asp Leu Leu Thr
                165                 170                 175

Ala Pro Glu Asp His Val Asp Leu Asp Lys Phe Ser Leu Asn Lys His
            180                 185                 190

His Leu Ile Val Val Tyr Lys Thr Ala Phe Tyr Ser Phe Tyr Leu Pro
        195                 200                 205

Val Ala Leu Ala Met Arg Met Val Gly Val Thr Asp Glu Glu Ala Tyr
    210                 215                 220

Lys Leu Ala Leu Ser Ile Leu Ile Pro Met Gly Glu Tyr Phe Gln Val
225                 230                 235                 240

Gln Asp Asp Val Leu Asp Ala Phe Arg Pro Pro Glu Ile Leu Gly Lys
                245                 250                 255

Ile Gly Thr Asp Ile Leu Asp Asn Lys Cys Ser Trp Pro Ile Asn Leu
            260                 265                 270

Ala Leu Ser Pro Ala Ser Pro Ala Gln Arg Glu Ile Leu Asp Thr Ser
        275                 280                 285

Tyr Gly Gln Lys Asn Ser Glu Ala Glu Ala Arg Val Lys Ala Leu Tyr
    290                 295                 300

Ala Glu Leu Asp Ile Gln Gly Lys Phe Asn Ala Tyr Glu Gln Gln Ser
305                 310                 315                 320

Tyr Glu Ser Leu Asn Lys Leu Ile Asp Ser Ile Asp Glu Lys Ser
                325                 330                 335

Gly Leu Lys Lys Glu Val Phe His Ser Phe Leu Gly Lys Val Tyr Lys
            340                 345                 350

Arg Ser Lys
        355

<210> SEQ ID NO 11
<211> LENGTH: 26
<212> TYPE: DNA
<213> ORGANISM: Artificial Sequence
<220> FEATURE:
```

```
<223> OTHER INFORMATION: Description of Artificial Sequence: Degenerate
      sense primer for cloning of HMC
<221> NAME/KEY: misc_feature
<223> OTHER INFORMATION: n = a, c, g or t
      r = a or g
      y = c or t
      h = a, t, or c

<400> SEQUENCE: 11
ggnaartaya cnathggnyt nggnca                                       26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Degenerate
      antisense primer for cloning of HMC gene
<221> NAME/KEY: misc_feature
<223> OTHER INFORMATION: n = a, c, g or t
      r = a or g
      s = c or g
      w = a or t

<400> SEQUENCE: 12
tanarnswns wngtrtacat rttncc                                       26

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primary
      primer for cloning of 5'-adjacent region of HMC gene

<400> SEQUENCE: 13
gaagaacccc atcaaaagcc tcga                                         24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Nested
      primer for cloning of 5'-adjacent region of HMC gene

<400> SEQUENCE: 14
aaaagcctcg agatccttgt gagcg                                        25

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Sense
      primer for cloning of small EcoRI portion of HMC gene

<400> SEQUENCE: 15
agaagccaga agagaaaa                                                18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Antisense
      primer for cloning of small EcoRI portion of HMC gene

<400> SEQUENCE: 16
```

```
tcgtcgagga aagtagat                                                    18
```

```
<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Sense
      primer for cloning of cDNA of HMC gene

<400> SEQUENCE: 17
ggtaccatat gtatccttct actaccgaac                                       30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Antisense
      primer for cloning of cDNA of HMC gene

<400> SEQUENCE: 18
gcatgcggat cctcaagcag aagggacctg                                       30

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Degenerate
      sense primer for cloning HMG gene
<221> NAME/KEY: misc_feature
<223> OTHER INFORMATION: n = a, c, g or t
      r = a or g
      y = c or t
      h = a, t, or c

<400> SEQUENCE: 19
gcntgytgyg araaygtnat hggntayatg cc                                    32

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Degenerate
      antisense primer for cloning of HMG gene
<221> NAME/KEY: misc_feature
<223> OTHER INFORMATION: n = a, c, g or t
      r = a or g
      y = c or t
      d = a, g, or t

<400> SEQUENCE: 20
atccarttda tngcngcngg yttyttrtcn gt                                    32

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Antisense
      primer for cloning of cDNA of HMG gene

<400> SEQUENCE: 21
ggccattcca cacttgatgc tctgc                                            25
```

```
<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Sense
      primer for cloning of cDNA of HMG gene

<400> SEQUENCE: 22
ggccgatatc tttatggtcc t                                          21

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Sense
      primer for cloning of cDNA of HMG gene

<400> SEQUENCE: 23
ggtaccgaag aaattatgaa gagtgg                                     26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Antisense
      primer for cloning of cDNA of HMG gene

<400> SEQUENCE: 24
ctgcagtcag gcatccacgt tcacac                                     26

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Degenerate
      sense primer for cloning of MVK gene
<221> NAME/KEY: misc_feature
<223> OTHER INFORMATION: n = a, c, g or t
      r = a or g
      y = c or t
      h = a, t, or c

<400> SEQUENCE: 25
gcnccnggna argtnathyt nttyggnga                                  29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Degenerate
      antisense primer for cloning of MVK gene
<221> NAME/KEY: misc_feature
<223> OTHER INFORMATION: n = a, c, g or t
      r = a or g
      s = c or g
      w = a or t

<400> SEQUENCE: 26
ccccangtns wnacngcrtt rtcnacncc                                  29

<210> SEQ ID NO 27
<211> LENGTH: 17
<212> TYPE: DNA
<213> ORGANISM: Artificial Sequence
```

```
<220> FEATURE:
<223> OTHER INFORMATION: Description of Artificial Sequence: Sense
      primer for cloning of genomic DNA containing MVK gene

<400> SEQUENCE: 27
acatgctgta gtccatg                                                        17

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Antisense
      primer for cloning of genomic DNA containing MVK gene

<400> SEQUENCE: 28
actcggattc catgga                                                         16

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Primer for
      genomic walking to clone 5'-adjacent region of MVK gene

<400> SEQUENCE: 29
ttgttgtcgt agcagtgggt gagag                                               25

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Sense
      primer for cloning of 5'-adjacent region of MVK gene

<400> SEQUENCE: 30
ggaagaggaa gagaaaag                                                       18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Antisense
      primer for cloning of 5'-adjacent region of MVK gene

<400> SEQUENCE: 31
ttgccgaact caatgtag                                                       18

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Sense
      primer for introduction of a nucleotide into MVK gene

<400> SEQUENCE: 32
ggatccatga gagcccaaaa agaaga                                              26

<210> SEQ ID NO 33
<211> LENGTH: 26
<212> TYPE: DNA
<213> ORGANISM: Artificial Sequence
<220> FEATURE:
```

```
<223> OTHER INFORMATION: Description of Artificial Sequence: Antisense
      primer for introduction of a nucleotide into MVK gene

<400> SEQUENCE: 33
gtcgactcaa gcaaaagacc aacgac                                              26

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Degenerate
      sense primer for cloning of MPD gene
<221> NAME/KEY: misc_feature
<223> OTHER INFORMATION: n = a, c, g or t
      r = a or g
      y = c or t
      h = a, t, or c
      m = a or c

<400> SEQUENCE: 34
htnaartayt tgggnaarmg nga                                                 23

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Degenerate
      antisense primer for cloning of MPD gene
<221> NAME/KEY: misc_feature
<223> OTHER INFORMATION: n = a, c, g or t
      r = a or g

<400> SEQUENCE: 35
gcrttnggnc cngcrtcraa ngtrtangc                                           29

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Sense
      primer for colony PCR to clone a genomic MPD clone

<400> SEQUENCE: 36
ccgaactctc gctcatcgcc                                                     20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Antisense
      primer for colony PCR to clone a genomic MPD clone

<400> SEQUENCE: 37
cagatcagcg cgtggagtga                                                     20

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Degenerate
      sense primer for cloning of FPS gene
<221> NAME/KEY: misc_feature
<223> OTHER INFORMATION: n = a, c, g or t
      r = a or g
```

```
        y = c or t

<400> SEQUENCE: 38
cargcntayt tyytngtngc ngayga                                          26

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Degenerate
      antisense primer for cloning of FPS gene
<221> NAME/KEY: misc_feature
<223> OTHER INFORMATION: n = a, c, g or t
      r = a or g
      y = c or t
      d = a, g or t

<400> SEQUENCE: 39
cayttrttrt cytgdatrtc ngtnccdaty tt                                   32

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Sense
      primer for cloningof FPS downstream region

<400> SEQUENCE: 40
atcctcatcc cgatgggtga atact                                           25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Antisense
      primer for cloning of FPS upstream region

<400> SEQUENCE: 41
aggagcggtc aacagatcga tgagc                                           25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Sense
      primer for cloning of cDNA and genomic FPS gene

<400> SEQUENCE: 42
gaattcatat gtccactacg cctga                                           25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Antisense
      primer for cloning of cDNA and genomic FPS gene

<400> SEQUENCE: 43
gtcgacggta cctatcactc ccgcc                                           25
```